United States Patent
Sivan et al.

(10) Patent No.: US 8,864,970 B2
(45) Date of Patent: Oct. 21, 2014

(54) METHODS AND DEVICES OF SEPARATING MOLECULAR ANALYTES

(75) Inventors: Uri Sivan, Haifa (IL); Elad Brod, Tivon (IL)

(73) Assignee: Technion Research & Development Foundation Limited, Haifa (IL)

( * ) Notice: Subject to any disclaimer, the term of this patent is extended or adjusted under 35 U.S.C. 154(b) by 115 days.

(21) Appl. No.: 13/390,539

(22) PCT Filed: Aug. 18, 2010

(86) PCT No.: PCT/IL2010/000671
§ 371 (c)(1),
(2), (4) Date: Feb. 15, 2012

(87) PCT Pub. No.: WO2011/021195
PCT Pub. Date: Feb. 24, 2011

(65) Prior Publication Data
US 2012/0145548 A1 Jun. 14, 2012

Related U.S. Application Data

(60) Provisional application No. 61/272,110, filed on Aug. 18, 2009, provisional application No. 61/349,919, filed on May 31, 2010.

(51) Int. Cl.
*C07K 1/28* (2006.01)
*G01N 27/447* (2006.01)

(52) U.S. Cl.
CPC ............ *G01N 27/44795* (2013.01); *C07K 1/28* (2013.01)

USPC ........... 204/459; 204/610; 204/458; 204/644; 422/82.01; 422/68.1; 435/287.1

(58) Field of Classification Search
USPC ......................... 204/548, 459, 610, 644, 450; 422/82.01, 68.1; 435/287.1
See application file for complete search history.

(56) References Cited

U.S. PATENT DOCUMENTS

| 4,868,130 A | 9/1989 | Hargreaves |
| 4,900,414 A | 2/1990 | Sibalis |
| 5,091,070 A | 2/1992 | Bauer et al. |

(Continued)

FOREIGN PATENT DOCUMENTS

| CN | 1462368 | 12/2003 |
| CN | 1549924 | 11/2004 |

(Continued)

OTHER PUBLICATIONS

Office Action Dated Jan. 14, 2013 From the Israel Patent Office Re. Application No. 204182 and Its Translation Into English.

(Continued)

*Primary Examiner* — Jennifer Dieterle

(57) ABSTRACT

A method of separating a mixture of a plurality of molecular analytes having different isoelectric points (pIs). The method comprises placing a solution containing a mixture of a plurality of molecular analytes in a separation volume, generating a pH profile having a plurality of pH zones across an axis of the separation volume, and adjusting a profile of the pH profile to induce a migration of a first molecular analyte along the axis apart from a second molecular analyte. The first and second molecular analytes having different pIs.

22 Claims, 16 Drawing Sheets

(56) References Cited

U.S. PATENT DOCUMENTS

| | | | |
|---|---|---|---|
| 5,110,434 A * | 5/1992 | Zhu et al. | 204/451 |
| 5,646,001 A | 7/1997 | Terstappen et al. | |
| 6,296,752 B1 | 10/2001 | McBride et al. | |
| 6,824,740 B1 | 11/2004 | Sheldon, III et al. | |
| 7,166,202 B2 | 1/2007 | Bukshpan et al. | |
| 8,366,899 B2 * | 2/2013 | Albrecht et al. | 204/548 |
| 2001/0023825 A1 | 9/2001 | Frumin et al. | |
| 2003/0102215 A1 | 6/2003 | Bukshpan et al. | |
| 2004/0101973 A1 | 5/2004 | Weber | |
| 2004/0231986 A1 | 11/2004 | Rossier et al. | |
| 2005/0126911 A1 * | 6/2005 | Anderson et al. | 204/470 |
| 2005/0189237 A1 | 9/2005 | Sano | |
| 2005/0284762 A1 | 12/2005 | Astorga-Wells et al. | |
| 2006/0029978 A1 | 2/2006 | O'Neill et al. | |
| 2006/0137603 A1 * | 6/2006 | Bukshpan | 117/68 |
| 2006/0169575 A1 | 8/2006 | Sumita | |
| 2012/0138468 A1 | 6/2012 | Sivan et al. | |
| 2013/0140182 A1 | 6/2013 | Paulus et al. | |

FOREIGN PATENT DOCUMENTS

| | | | |
|---|---|---|---|
| CN | 1558460 | | 12/2004 |
| CN | 101294930 | | 10/2008 |
| EP | 688395 | | 8/2006 |
| JP | 2002-265494 | | 9/2002 |
| JP | 2006-213932 | | 8/2006 |
| JP | 2006-247640 | | 9/2006 |
| JP | 2007-190548 | | 8/2007 |
| WO | WO 91/17815 | | 11/1991 |
| WO | WO 02/25263 | | 3/2002 |
| WO | WO 03/008977 | | 1/2003 |
| WO | WO 2005/021841 | * | 3/2005 |
| WO | WO 2007/093395 | | 8/2007 |
| WO | WO 2008/112253 | | 9/2008 |
| WO | WO 2008/131328 | | 10/2008 |
| WO | WO 2009/002459 | * | 12/2008 |
| WO | WO 2009/027970 | | 3/2009 |
| WO | WO 2011/021196 | | 2/2011 |

OTHER PUBLICATIONS

Communication Under Rule 71(3) EPC Dated Oct. 11, 2013 From the European Patent Office Re. Application No. 08789831.8.
Communication Pursuant to Article 94(3) EPC Dated Jul. 20, 2010 From the European Patent Office Re. Application No. 08789831.8.
Communication Pursuant to Article 94(3) EPC Dated Mar. 24, 2011 From the European Patent Office Re. Application No. 08789831.8.
Communication Pursuant to Article 94(3) EPC Dated Jul. 26, 2011 From the European Patent Office Re. Application No. 08789831.8.
Communication Pursuant to Article 94(3) EPC Dated Sep. 28, 2010 From the European Patent Office Re. Application No. 08789831.8.
Communication Relating to the Results of the Partial International Search Dated Dec. 20, 2010 From the International Searching Authority Re. Application No. PCT/IL2010/000672.
International Preliminary Report on Patentability Dated Mar. 2, 2010 From the International Bureau of WIPO Re.: Application No. PCT/IL2008001159.
International Search Report and the Written Opinion Dated Apr. 7, 2009 From the International Searching Authority Re.: Application No. PCT/IL2008/001159.
International Search Report and the Written Opinion Dated Dec. 10, 2010 From the International Searching Authority Re.: Application No. PCT/IL2010/000671.
International Search Report and the Written Opinion Dated Mar. 24, 2011 From the International Searching Authority Re.: Application No. PCT/IL2010/000672.
Response Dated Jul. 4, 2011 to Communication Pursuant to Article 94(3) EPC of Mar. 24, 2011 From the European Patent Office Re. Application No. 08789831.8.
Response Dated Mar. 9, 2011 to Communication Pursuant to Article 94(3) EPC of Sep. 28, 2010 From the European Patent Office Re. Application No. 08789831.8.
Response Dated Sep. 16, 2010 to Communication Pursuant to Article 94(3) EPC of Jul. 20, 2010 From the European Patent Office Re. Application No. 08789831.8.
Response Dated Nov. 21, 2011 to Communication Pursuant to Article 94(3) EPC of Jul. 26, 2011 From the European Patent Office Re. Application No. 08789831.8.
Translation of Office Action Dated Nov. 9, 2011 From the State Intellectual Property Office of the People's Republic of China Re. Application No. 200880114690.6.
Britz-McKibbin et al. "Selective Focusing of Catecholamines and Weakly Acidic Compounds by Capillary Electrophoresis Using a Dynamic pH Junction", Analytical Chemistry, XP002611194, 72(6): 1242-1252, Mar. 15, 2000. p. 1250, col. 1, Line 22—p. 1251, col. 1, Line 1, Fig.9.
Pabst et al. "Separation of Protein Charge Variants With Induced pH Gradients Using Anion Exchange Chromatographic Columns", Biotechnology Progress, XP002611195, 24(5): 1096-1106, Sep. 2008. Abstract, p. 1100, col. 1, Lines 12-16.
Wu et al. "Isoelectric Focusing Sample Injection for Capillary Electrophoresis of Proteins", Electrophoresis, XP002611196, 26(3): 563-570, Feb. 2005. Abstract, p. 565, col. 2, Last §—p. 566, col. 1, Last §, p. 567, col. 1, Line 17—col. 2, Line 11, Fig.3B.
Wu et al. "Miniaturization of Capillary Isoelectric Focusing", Electrophoresis, XP003008375, 22: 3968-3971, Jan. 1, 2001. Abstract, p. 3669, col. 2, Line 1—p. 3970, col. 1, Last Line, Figs. 1, 3, 4.
International Preliminary Report on Patentability Dated Mar. 1, 2012 From the International Bureau of WIPO Re. Application No. PCT/IL2011/000671.
Partial European Search Report and the European Search Opinion Dated Mar. 5, 2013 From the European Patent Office Re. Application No. 12177368.3.
Huang et al. "Capillary Isoelectric Focusing Without Carrier Ampholytes", Analytical Chemistry, XP002584974, 72(19): 4758-4761, Oct. 1, 2000. Abstract, Fig. 1.
Examiner's Report Dated Feb. 27, 2012 From the Australian Government, IP Australia Re. Application No. 2008293381.
Translation of Reason for Rejection Dated Jul. 2, 2013 From the Japanese Patent Office Re. Application No. 2010-522513.
Translation of Notification of Office Action Dated Jul. 29, 2013 From the State Intellectual Property Office of the People's Republic of China Re. Application No. 201080036972.6.
Translation of Search Report Dated Jul. 29, 2013 From the State Intellectual Property Office of the People's Republic of China Re. Application No. 201080036972.6.
Restriction Official Action Dated Sep. 19, 2012 From the US Patent and Trademark Office Re. U.S. Appl. No. 12/675,794.
Invitation Pursuant to Rule 62a(1) EPC Dated Nov. 23, 2012 From the European Patent Office Re. Application No. 12177368.3.
Official Action Dated Nov. 16, 2012 From the US Patent and Trademark Office Re. U.S. Appl. No. 12/675,794.
International Preliminary Report on Patentability Dated Mar. 1, 2012 From the International Bureau of WIPO Re. Application No. PCT/IL2010/000672.
Communication Pursuant to Rules 70(2) and 70a(2) EPC and Reference to Rule 39(1) EPC Dated Apr. 8, 2013 From the European Patent Office Re. Application No. 12177368.3.
Translation of Office Action Dated May 2, 2012 From the State Intellectual Property Office of the People's Republic of China Re. Application No. 200880114690.6.
Official Action Dated Jun. 6, 2013 From the US Patent and Trademark Office Re. U.S. Appl. No. 12/675,794.
Translation of Notice of Reason for Rejection Dated Jul. 27, 2012 From the Japanese Patent Office Re. Application No. 2010-522513.
Restriction Official Action Dated Oct. 7, 2013 From the US Patent and Trademark Office Re. U.S. Appl. No. 13/390,352.
Notification of the Office Action Dated Sep. 18, 2013 From the State Intellectual Property Office of the People's Republic of China Re. Application No. 201080036971.1 and Its Translation Into English.
Search Report Dated Sep. 18, 2013 From the State Intellectual Property Office of the People's Republic of China Re. Application No. 201080036971.1 and Its Translation Into English.

(56) References Cited

OTHER PUBLICATIONS

Translation of Notice of Reason for Rejection Dated Sep. 20, 2013 From the Japanese Patent Office Re. Application No. 2012-525252.
Dismissal of Amendment Dated Mar. 14, 2014 From the Japanese Patent Office Re. Application No. 2010-522513 and Its Translation Into English.
Official Decision of Rejection Dated Mar. 14, 2014 From the Japanese Patent Office Re. Application No. 2010-522513 and Its Translation Into English.
Official Action Dated Sep. 10, 2013 From the US Patent and Trademark Office Re. U.S. Appl. No. 13/669,023.
De Jong et al. "Membranes and Microfluidics: A Review", Lab on a Chip, 6(9): 1125-1139, Sep. 2006.
Notification of the Office Action Dated May 8, 2014 From the State Intellectual Property Office of the People's Republic of China Re. Application No. 201080036971.1 and Its Translation Into English.
Communication Under Rule 71(3) EPC Dated Feb. 4, 2014 From the European Patent Office Re. Application No. 12177368.3.
Notification of Office Action Dated Jan. 9, 2014 From the State Intellectual Property Office of the People's Republic of China Re. Application No. 201080036972.6 and Its Translation Into English.
Notice of Reason for Rejection Dated Jan. 7, 2014 From the Japanese Patent Office Re. Application No. 2012-525253 and Its Translation Into English.
Official Action Dated Jan. 16, 2014 From the US Patent and Trademark Office Re. U.S. Appl. No. 13/390,352.
Office Action Dated Feb. 20, 2014 From the State Intellectual Property Office of the People's Republic of China Re. Application No. 201210450797.6 and Its Translation Into English.
Search Report Dated Feb. 20, 2014 From the State Intellectual Property Office of the People's Republic of China Re. Application No. 201210450797.6 and Its Translation Into English.
Notice of Reason for Rejection Dated Jun. 6, 2014 From the Japanese Patent Office Re. Application No. 2012-525252 and Its Translation Into English.
Official Action Dated Jul. 11, 2014 From the US Patent and Trademark Office Re. U.S. Appl. No. 12/675,794.
Official Action Dated Aug. 13, 2014 From the US Patent and Trademark Office Re. U.S. Appl. No. 13/390,352.
Patent Examination Report Dated Jun. 5, 2014 From the Australian Government, IP Australia Re. Application No. 2010286046.
Patent Examination Report Dated Jul. 30, 2014 From the Australian Government, IP Australia Re. Application No. 2010286047.

* cited by examiner

METHODS AND DEVICES OF SEPARATING MOLECULAR ANALYTES

RELATED APPLICATIONS

This application incorporates by reference International Patent Application No. PCT/IL2008/001159 filed on Aug. 26, 2008 (PCT Publication No. WO2009/027970 published on Mar. 5, 2009), U.S. Provisional Patent Application No. 61/272,110 filed on Aug. 18, 2009 and U.S. Provisional Patent Application No. 61/349,919 filed on May 31, 2010.

This application is a National Phase of PCT Patent Application No. PCT/IL2010/000671 having International filing date of Aug. 18, 2010, which claims the benefit of priority of U.S. Provisional Patent Application No. 61/272,110 filed on Aug. 18, 2009 and U.S. Provisional Patent Application No. 61/349,919 filed on May 31, 2010. The contents of the above applications are all incorporated herein by reference.

FIELD AND BACKGROUND OF THE INVENTION

The present invention, in some embodiments thereof, relates to molecular analysis and separation and, more particularly, but not exclusively, to methods molecular analysis and separation using electrofocusing.

Isoelectric focusing is an analytical technique for separating molecules in an analyte sample by taking advantage of the differing ionic properties of the molecules.

Isoelectric focusing is usually performed in an electrolyte solution, optionally in a gel form, for example based on polyacrylamide, starch and/or agarose, having an immobilized proton concentration gradient, generally the proton concentration gradient changing from higher to lower pH in a given direction. In some implementation solutions which contain ampholytes which, under an electric field, generate a pH profile. In isoelectric focusing, the separation takes place in a pH profile that occupies the whole separation distance and is arranged so that the pH in the gradient increases from anode towards the cathode. In use, the analyte is loaded onto some location on the electrolyte solution. The charge of each different molecule changes in response to the ambient proton concentration according to the acidity (pKa) of the various functional groups of the molecule.

An electric potential is applied parallel to the proton concentration gradient between an isoelectric focusing anode and isoelectric focusing cathode. Molecules having a net positive charge migrate through the electrolyte solution towards the cathode while molecules having a net negative charge migrate through the electrolyte solution towards the anode.

As the molecules migrate, the ambient pH change to reduce the net charge on the molecule until the molecule reaches an isoelectric point (pI) where, due to the ambient pH, the net charge on the molecule is zero. The pI is the pH at which a particular molecule or surface carries no net electrical charge. In this point the migrating molecule stops since they have zero charge. In such a manner, isoelectric focusing focuses molecules having a certain pI into a relatively narrow volume of the electrolyte solution. Isoelectric focusing is useful for the analysis of proteins by characterizing them according to their acidities. More importantly, it is useful for separation of protein mixtures.

International Patent Application Publication No. WO 2009/027970, published on Mar. 5, 2009 and incorporated herein by reference, describes methods and devices useful in producing local concentrations of protons, proton concentration gradients and desired proton concentration topographies in an environment, such as an electrolyte solution, a gel, or the like, including an electrolyte. This application also discloses methods and devices for isoelectric focusing.

SUMMARY OF THE INVENTION

According to some embodiments of the present invention there is provided a method of separating a mixture of a plurality of molecular analytes having different isoelectric points (pIs). The method comprises placing a solution containing a mixture of a plurality of molecular analytes in a separation volume, generating a pH profile having a plurality of pH zones across an axis of the separation volume, and adjusting a profile of the pH profile to induce a migration of a first of the plurality of molecular analytes along the axis apart from a second of the plurality of molecular analytes, the first and second molecular analytes having different pIs.

Optionally, the pH profile having at least two pH step zones having different pH levels, the plurality of molecular analytes being trapped between the at least two pH step zones having a substantially uniform pH before the adjusting, the adjusting comprising changing the pH in one of the at least two pH step zones.

Optionally, the adjusting is performed gradually in time.

Optionally, the pH profile is defined by at least one ramp, the plurality of molecular analytes accumulating in the at least one ramp.

Optionally, the generating comprises applying an electric field on the solution along the axis, and injecting a plurality of ion flows in a plurality of points along the axis to establish the pH profile.

Optionally, the method comprises adding at least one buffer element to the solution so as to stabilize the pH profile.

Optionally, the method comprises collecting the first molecular analyte while the second molecular analyte remain in the separation volume.

Optionally, the method comprises adjusting the profile to induce a migration of the second molecular analyte along the axis apart from a third of the plurality of molecular analytes, the second and third molecular analytes having different pIs.

Optionally, the adjusting comprises adjusting the profile to induce a migration of the first and second molecular analytes in opposite directions along the axis.

Optionally, the adjusting comprises adjusting the profile to change a direction of the migration along the axis so that the first molecular analyte sequentially drifting in two opposing directions.

Optionally, the plurality of pH zones having two step zones having a substantially uniform first pH separated by a middle step zone having a substantially uniform second pH, the mixture being trapped in between one of the two step zones and the middle step zone, the adjusting comprising changing the pH in the middle step zones.

Optionally, the plurality of pH zones comprises at least three different pH zones, the adjusting being performed gradually so as to induce a migration of the first molecular analyte to a first ramp zone between a first pair of the plurality of pH zones and the second molecular analyte to a second ramp zone between a second pair of the plurality of pH zones.

Optionally, the solution is buffered.

Optionally, the method comprises providing an isoelectric point of one or more molecular analytes in the mixture and setting the solution according to isoelectric point determining a buffer concentration of the solution according to the isoelectric point and setting the solution according to the determining.

Optionally, the adjusting comprises focusing the first and second molecular analytes apart from one another along the axis.

More optionally, further comprising separately collecting the first and second focused molecular analytes from different locations along the axis.

Optionally, the generating comprises calculating the pH profile according to a set of algebraic equations.

Optionally, the adjusting comprises calculating at least one adjustment for the pH profile according to a set of algebraic equations and performing the adjusting according to the at least one adjustment.

According to some embodiments of the present invention there is provided a method of separating a mixture of a plurality of molecular analytes having different isoelectric points (pIs). The method comprises placing a solution containing a mixture of a plurality of molecular analytes in a separation volume, trapping the plurality of molecular analytes in between two pH step zones in a separation volume containing the solution, each the pH step zone having a different substantially uniform pH, and gradually changing a pH in one of the two pH step zones to induce a sequential migration of the plurality of molecular analytes in a plurality of separate groups each the group having a different pI.

Optionally, the trapping comprises applying an electric field on the solution and injecting a plurality of ion flows in at least one point along to establish the two pH step zones.

According to some embodiments of the present invention there is provided a method of separating molecular analytes based on their isoelectric point. The method comprises generating a pH profile having a plurality of pH zones in a solution having a plurality of molecular analytes and gradually changing the profile of the pH profile over a period to induce a spatial separation of the plurality of molecular analytes according to their respective isoelectric points.

According to some embodiments of the present invention there is provided a device of separating a mixture of a plurality of molecular analytes having different isoelectric points (pIs). The device comprises a container sized and shaped contains a solution having a plurality of molecular analytes along an axis, an electric source of applying an electric field along an axis in the solution, a plurality of ion sources for establish a pH profile along the axis in the solution by injecting a plurality of ion flows to at least one of protonating and deprotonating a plurality of zones of the solution, and a controller which operates the plurality of ion sources to gradually adjust the pH profile so as to induce a migration of each the molecular analyte separately along the axis.

Optionally, the device further comprises an interface for receiving a plurality of instructions from at least one of a computing unit and a user, the controller operating the plurality of ion sources according to the plurality of instructions.

Optionally the container having at least one dimension of less than one millimeter.

Optionally the solution is a non gel solution.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 10B-D and FIGS. 10E-H respectively depict a dynamic pH profile along an axis, such as depicted in FIG. 10A and FIG. 10E, according to some embodiments of the present invention;

DESCRIPTION OF EMBODIMENTS OF THE INVENTION

Figure 1:
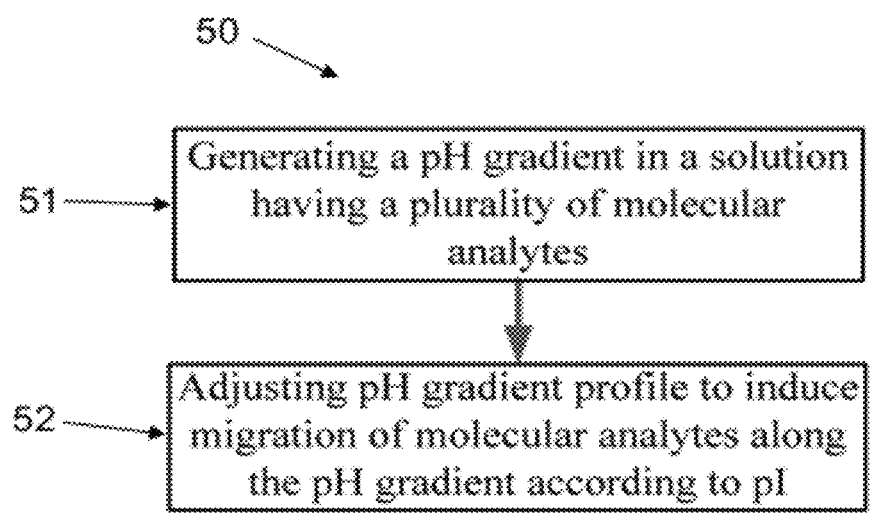
FIG. 1, which is a flowchart of method of separating molecular analytes based on their isoelectric point, according to some embodiments of the present invention.

The present invention, in some embodiments thereof, relates to molecular analysis and separation and, more particularly, but not exclusively, to methods molecular analysis and separation using electrofocusing.

According to some embodiments of the present invention, there is provided methods and devices of temporally separating a mixture of molecular analytes having different isoelectric points (pIs). The method is based on generating a pH profile having different pH zones in a separation volume that includes a solution with a mixture of molecular analytes, such as proteins. After a pH profile, optionally graduated is formed, its profile is gradually changed over a period to induce a spatial separation of the molecular analytes according to their respective pIs. Optionally, the profile is changed so as to induce a separate movement of having different pIs along a common axis, such as the pH profile axis. Molecular analytes with different pIs may drift simultaneously or sequentially in opposing directions and/or sequentially in a common direction. Optionally, the profile is changed by gradually increasing or decreasing the pH in one or more step zones having a substantially stable pH of the pH profile.

According to some embodiments of the present invention, a device of separating a mixture of a plurality of molecular analytes having different pIs is disclosed. The device includes a container that sized and shaped to contain a solution having a plurality of molecular analytes along an axis, for example a channel having an average diameter of about one millimeter or less, for example a channel having a cut profile of 100×3× 0.3 mm. The device further includes a high voltage power supply that applies an electric field along an axis in the solution, for example along the axis of the channel. The device further includes ion sources which are set to establish a pH profile along the axis in the solution by injecting ion flows which lower or raise the pH in certain zones of the separation volume, for example the ion sources may be as defined in U.S. Provisional Patent Application. No. 61/272,110 filed on Aug. 18, 2009. The ion sources are connected to a controller that operates the plurality of ion sources to gradually adjust the pH profile so as to induce a migration of each one of the molecular analytes separately along the axis, optionally sequentially. Optionally, the controller is connected to a computing unit and/or an interface, such as a manual interface, that allows a user to provide instructions for generating the pH profile and change it dynamically to induce molecular analytes migration.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a flowchart of a method 50 of separating molecular analytes based on their isoelectric point (pI), according to some embodiments of the present invention. As used herein, molecular analytes means molecules, biomolecules, such as proteins, peptides, peptide-based pharmaceutical compounds, and biomolecule based pharmaceutical compounds, and pH dependent objects such as colloids or any other charged molecule which can undergo protonation/deprotonation. The separation is performed along a separation volume, optionally in a solution that includes the molecular analytes, such as an electrolyte solution.

Figure 2A:
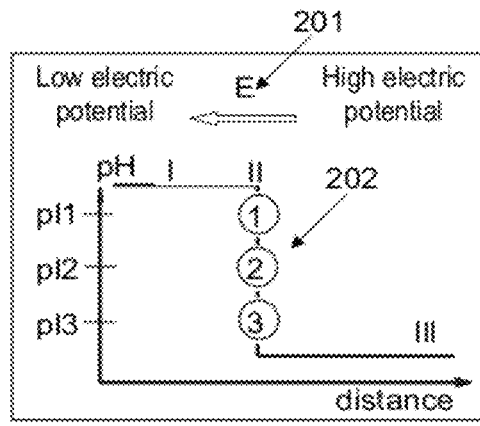
FIGS. 2A-2E are schematic graphical illustrations of a dynamic pH profile and its effect on molecular analytes which are in the solution in a container over a period, according to some embodiments of the present invention.

First, as shown at 51, a pH profile having different pH step zones is generated in a solution with a mixture of molecular analytes. The pH profile is formed across a certain axis, which may be referred to herein as a pH profile axis. An electric potential is applied along the pH profile axis to induce ion flow, for example as described below. The pH profile is formed so as to trap the molecules of the mixture in a pH ramp zone between the different pH step zones. For example, FIG. 2A depicts a pH profile where three molecular analytes, marked with the circled numerals 1, 2, and 3, are at a ramp between a high pH step zone and a low pH step zone. Optionally, the pH profile is generated using a device as described below in relation to FIG. 3A and FIG. 3B. Molecular analytes, such as proteins, are assumed to have a positive charge at low pH values, where the proton concentration is high, and negative charge at high pH values, where the proton concentration is low. The pH profile may be established by controlling the pH level along different zones of a container that contains the aforementioned solution, such as shown at numeral 102 of FIG. 3A and FIG. 3B. The control may be achieved by adjusting the proton concentration in the pH step zones Now, as shown at 52, the profile of the pH profile is adjusted to induce a migration of one or more of the molecular analytes based on their isoelectric points, for example along the pH profile axis. The adjustment of the pH profile mobilizes the molecular analytes based on their pI. Each molecular analyte drifts in along the pH profile axis until it reaches a pH zone in which its pH carries no net electrical charge. In this zone, the local pH equals to its pI so that the molecular analyte drift velocity is reduced to approximately null and the molecular analyte comes to a halt. As further described below, such a migration forms a plurality of separate groups of molecular analytes, having different pIs, across the pH profile axis. Optionally, the separation is based on the mobility characteristics of charged molecular analytes in the presence of an external electric field, for example its drift velocity. These characteristics are proportional to their charge, and thus vary along the changing pH in zones along the pH profile axis.

Optionally, the pH profile is temporally controlled. For example, the pH profile is gradually adjusted in monitored intervals along a period. As different molecular analytes with different pI have different drift velocities, their migration pace along the pH profile is different. As such, the time it takes a molecular analyte to travel a certain distance along the pH profile in a certain profile is indicative of its pI. As such, the order arrival of different molecular analytes to a certain target location along a pH profile having a certain profile is indicative of its relative pI value. Moreover, as the drift velocity of different molecular analytes is different, groups of molecular analytes may be separated by mobilizing them in different velocities along the pH profile axis in the separation volume.

As used herein, a pH profile that is controllably adjusted during a period of time is referred to as a dynamic pH profile. By establishing a dynamic pH profile in the separation volume, molecular analytes may be separated not spatially, namely separated to different pH zones but also in the temporally, namely separated to arrive at a common location in the separation volume in different time slots. For example, the changing of the pH profile as described above allows temporally separating the arrival of molecular analytes to a certain zone in the separation volume. This allows, as further described below, placing a probing unit to probe or a diagnostic unit to diagnose molecular analytes which are mobilized in front of it. When the pH profile is set in a certain static profile, molecular analytes are halt in a certain location therealong. When the profile of the pH profile is dynamically changed gradually, the molecular analytes are released sequentially as a time dependent pH change in a certain zone gives separation in time between the different molecules. By slow variation of the pH profile, the separation in release time of two molecules having close pI value from a certain pH ramp zone (the proteins are concentrated in the ramp zone before they are separated) may be made arbitrarily large, yielding separation of proteins characterized by an arbitrarily small pI difference. Such separation is attained spatially.

Figure 3A:
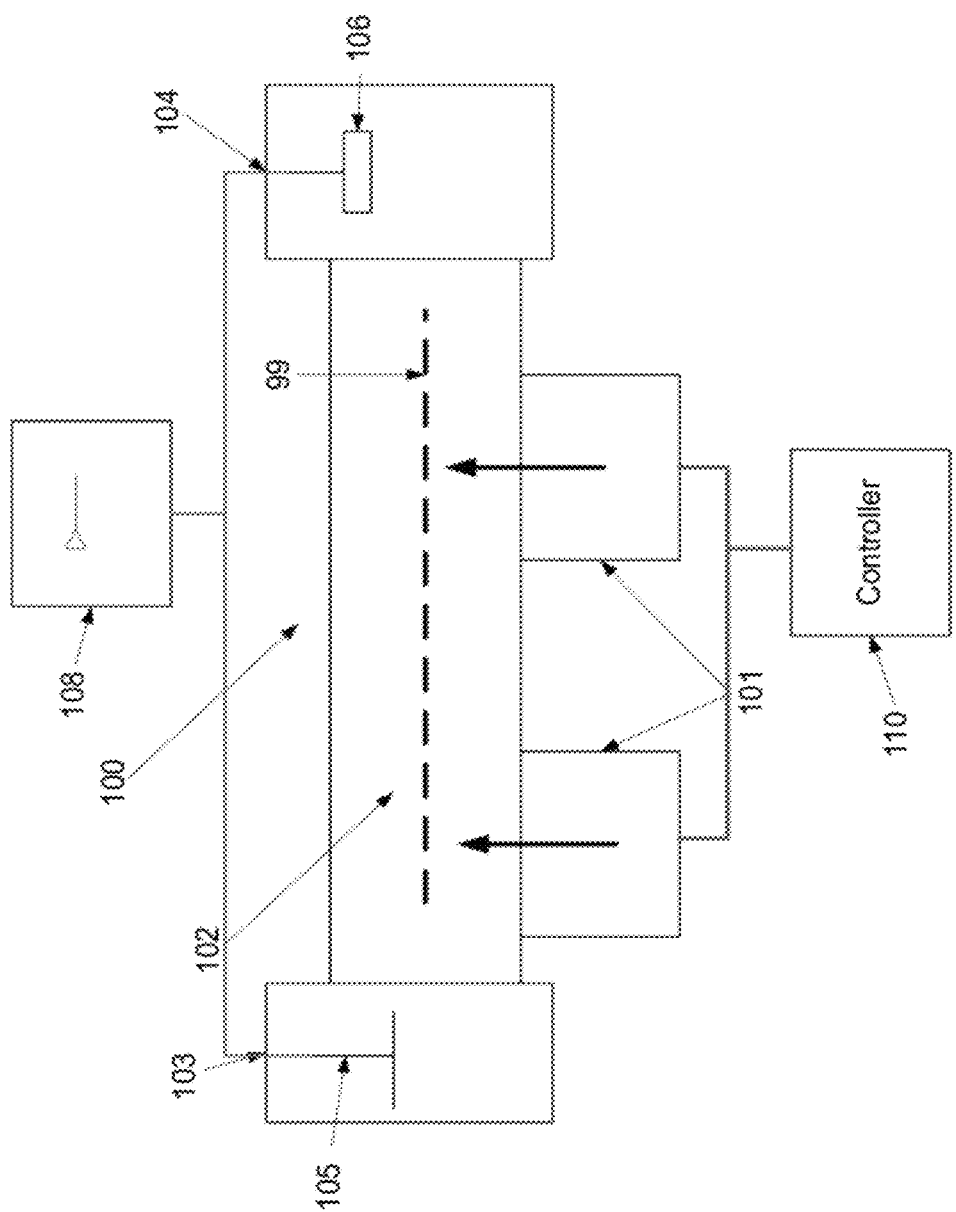
FIG. 3A is a schematic illustration of a lateral view of an exemplary separation device of separating molecular analytes in a separation volume based on their isoelectric point, according to some embodiments of the present invention.

Reference is now made to FIG. 3A, which is a schematic illustration of a lateral view of an exemplary separation device 100 of separating molecular analytes in a separation volume based on their isoelectric point (pI), according to some embodiments of the present invention. This separation allows separately diagnosing and/or collecting molecular analytes. The separation device 100 creates a spatio-temporal pH profile, a dynamic pH profile, having a time dependent pH trap in a solution. When the pH profile is adjusted by changing the pH on one of the pH step zones, some molecular analytes are released from the trap while others remain trapped. In such a manner, different molecular analytes may be separated from one another. The separation device 100 includes a plurality of ion sources 101 which are optionally arranged as an array in a close proximity to a container 102 that define a separation volume and contains a solution, such as an electrolyte solution. The container 102 may be referred to herein as a channel and/or a focusing channel. As further described below, the ion sources 101 are set to establish a pH profile in the solution by feeding the container 102 with a plurality of ion flows in a plurality of different zones of the container 102 where each ion flow changes the pH level of a different zone. Each ion source 101 changes the pH in a respective pH zone in the separation volume in the container 102 where the pH profile is established. Optionally, the ion sources 101 control the pH level at different zones along the pH profile axis that is parallel to a longitudinal axis 99 of the container 102, or any other axis that is parallel thereto, by generating ion flow and injecting it into the focusing channel 102. Optionally, the ion sources 101 are pH generators and the container is a focusing channel, for example as described in U.S. Provisional Patent Application No. 61/272,110 filed on Aug. 18, 2009, which is incorporated herein by reference.

As depicted in FIG. 3A each one of the left and right sides of the container 102 are connected to solution receptacle 103, 104 which may be referred to as feed reservoirs. One of the electrolyte solution receptacles 103 is connected to a cathode 105 and the other 104 is connected to an anode 106 which are connected to a high voltage power supply 108 and set to apply high voltage (HV) in the container 102, along the separation volume. Optionally, the system 100 further comprises a controller 110 that controls the main current source 108 and/or the ion sources 101, optionally separately. The controller 110 may change the pH profile by instructing some or all of the ion sources 101 to change the pH in respective zones, It should be noted that though only three ion sources 101 are depicted, the separation device 100 may have any number of ion sources 101, for example, 4, 8, 12, 16, 20, 100 or any intermediate or greater number.

Figure 3B:
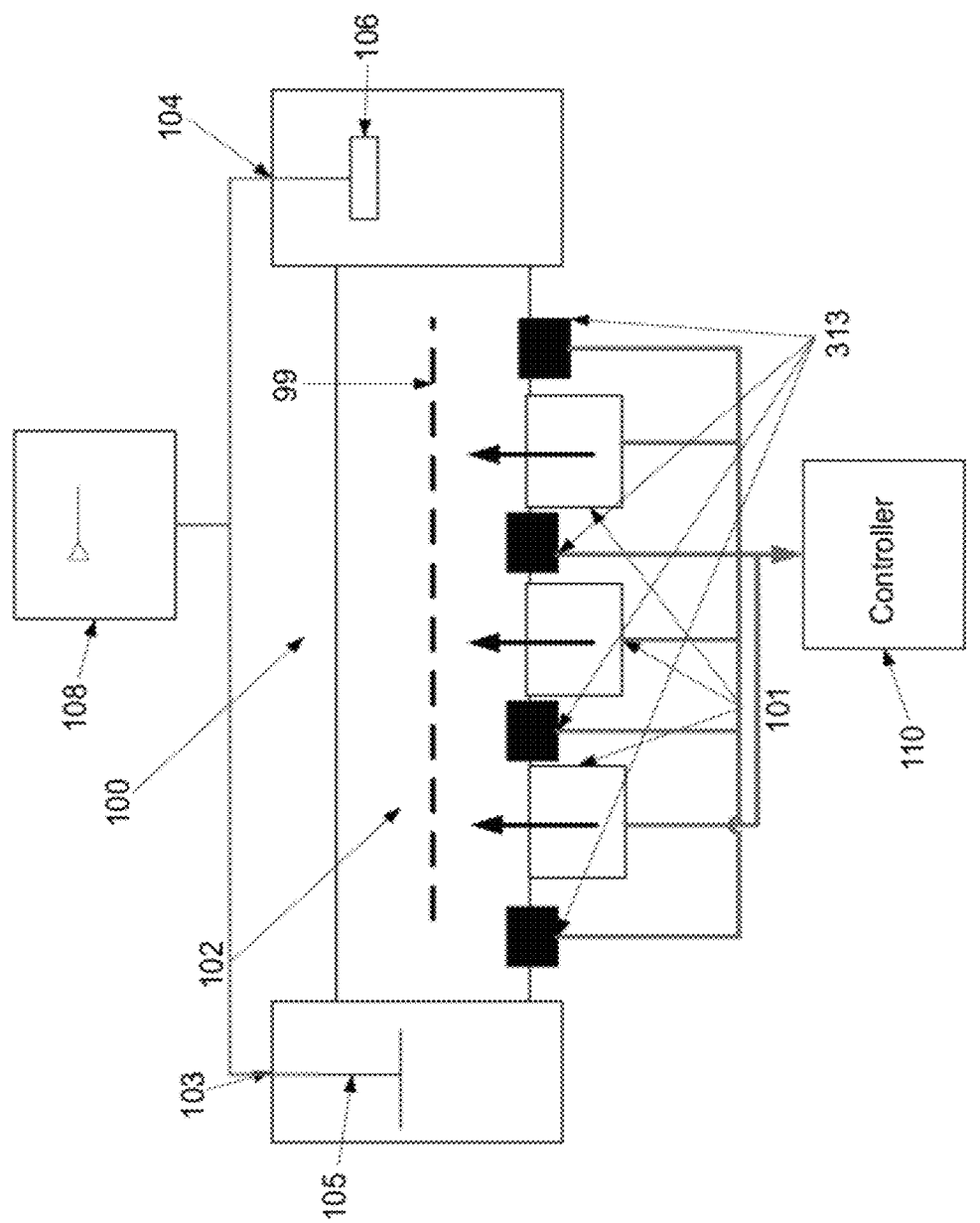
FIG. 3B is a schematic illustration of a lateral view of an exemplary separation device as depicted in FIG. 3A with an array of pH sensors which are along its channel, according to some embodiments of the present invention.

Optionally, as shown at FIG. 3B and described in Provisional Patent Application No. 61/272,110 filed on Aug. 18, 2009, which is incorporated herein by reference, an array of pH sensors 313 are placed along the channel, to close a feedback loop together with the controller 110 and proton/hydroxyl sources 101. In use, the channel 102 is filled with a solution, optionally selected as described below. Then, the controller is fed with instructions to form a desired dynamic pH profile, suited for the separation of a certain mixture that is added to the solution. Optionally, the controller 110 is connected to a user interface that allows manually providing the dynamic pH profile. In another embodiment, a computing unit (not shown) that is connected to the controller 110 computes the dynamic pH profile automatically, optionally using the equations below, for example based on the pI of the probed molecular analytes. Next, the HV power supply 108 is turned on to maintain a potential difference of, say, 300V, in the separation volume. The controller 110 than operates the ion sources 110 according to the user input/or computing unit, and, if pH sensors 313 are present, activates a feedback loop, to maintain the desired pH profile over time. When the latter is established, the mixture is inserted to the channel 102 through a loader, optionally located in one of the sides of the container 102. The molecular analytes than migrate according to the pH and the electric field inside the channel 102. As the latter moves and focus, the user resets the pH profile according to the desired dynamic pH profile. The controller 110 then operates the ion sources 101 according to the received instructions in real time. As used herein real time means adjusting pH profile without computing delays of more than few seconds. Finally, as further described below, migrating molecular analytes are separately collected through the harvesting unit or probed in a position along the channel. This separation device 100 has a number of advantageous features as compared to existing isoelectric focusing devices. For example, the devices allow using a gel and/or ampholyte free solution, facilitating higher purification yields and shorter purification times. Moreover, the separation device 100 could be designed so that each escaping molecule would travel only a short distance of about 1 millimeter (mm) until it is purified, making the purification times relatively short. In addition, in some of the separation strategies the molecules travel along a common trajectory, making the design and/or operation of the harvesting and/or diagnosing units simple. These units may be positioned at a defined point from where all the molecules can be withdrawn or probed. Finally, the pH profile may be suited time and/or space wise to make an optimal purification process to every bio-molecule mixture.

Such a separation device 100 may be used for separating molecular analytes by inducing the migration of some of them along the pH profile formed in the separation volume in the container 102.

For example, reference is now made to FIGS. 2A-2E, which are schematic graphical illustrations of a dynamic pH profile and its effect on molecular analytes which are in the solution in the container 102 over a period, according to some embodiments of the present invention. The two ion sources 101 are set to establish the pH profile depicted in FIG. 2A. As outlined above, FIG. 2A depicts three different molecular analytes at a pH ramp zone between a high pH step zone and a low pH step zone of a pH profile. The spatial dimensions of the three zones may be selected to measure from 10 micrometers to a number of centimeters (cm), for example 10 cm, 20 cm, 50 cm or any intermediate or larger number, while the typical dimension of a pH ramp zone is a few tens of micrometers. An electric field is applied at the direction shown by numeral 201, by the cathode 105 and the anode 106. The pH ramp zone 202 in the pH profile is defined by changing the pH in various zones of the container so that the pH levels are defined as follows:

$$pH(I) > pI1 > pI2 > pI3 > pH(III) \text{ and } pH(I) > pH(II) > pH(III)$$

where pH(I)-pH(III) respectively denotes the pH level in the high pH step zone, the pH ramp zone, and the low pH step zone, and pI1-pI3 respectively denote the pI of the first, second and third molecular analytes. In FIG. 2A, a mixture of three molecular analytes, for example three proteins, are concentrated in the pH ramp zone II after being injected into either step zone I or step zone III. The molecular analytes are assumed to have a negative electric charge if inserted to the high pH step zone such as zone I and hence drift opposite to the direction of the electric field toward lower pH step zones. If the molecular analytes are injected into a low pH step zone, such as zone III, they assumed as having a positive charge and hence drift in the direction of the electric field toward a higher pH step zones. In either case, the molecular analytes drift in the electric field formed in the solution towards the pH ramp zone, marked as pH ramp II, where they get trapped as their pI is at the pH level thereof and therefore they carry no electrical net charge. The molecules of the molecular analytes are trapped as the low pH step zone induces them to attain a positive charge and the high pH plateau induces them to attain a negative charge.

Figure 2B:
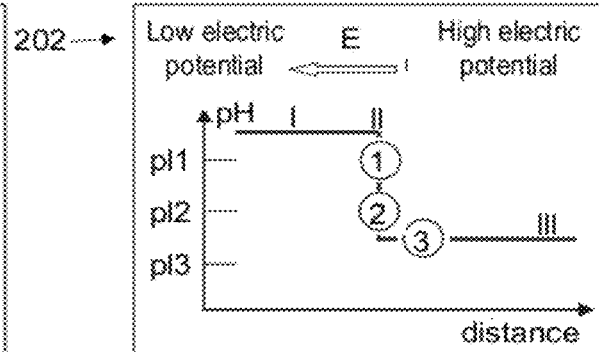
Figure 2C:
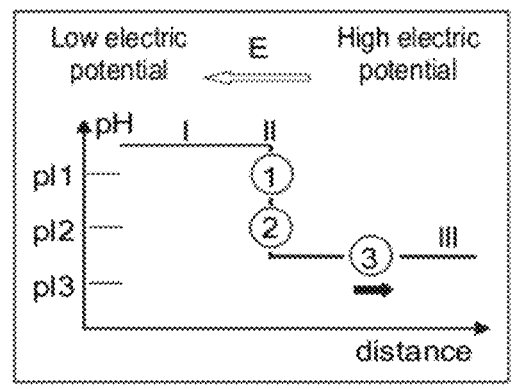
Figure 2D:
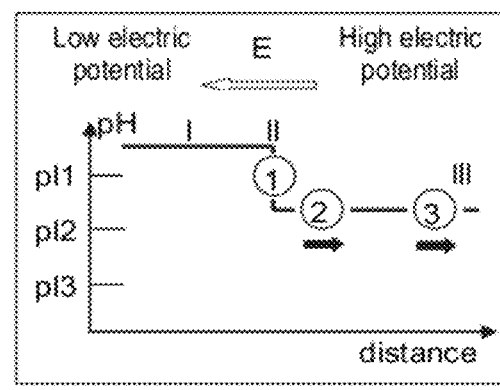
Figure 2E:
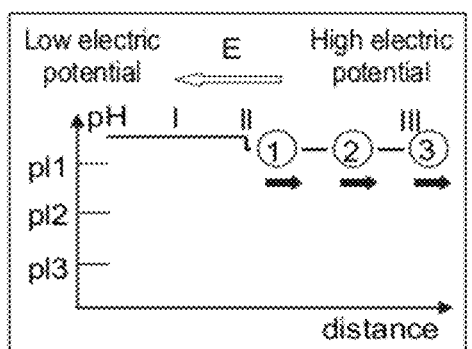

Now, as shown at FIG. 2B, the pH profile is adjusted to induce a migration of one of the molecular analytes. In the depicted example, the pH profile is changed so that the pH in zone III is increased to a value intermediate between pI3 and pI2, namely to a point where pH(I)>pI1>pI2>pH(III)>pI3. Under this profile, the third molecular analyte is negatively charged so as to drift from the pH ramp zone toward the right end of the low pH step zone of the pH profile, against the electric field flow direction, for example as shown at FIG. 2C. For clarity, the drift direction in FIGS. 2A-2E is marked with a solid arrow and the electric field is marked by an arrow with the marking E. At the same time, the first and second molecular analytes remain in the pH ramp zone. The third molecular analyte may now be collected and/or probed at the right hand side of the separation volume, for example of the container 102. To separate the second molecular analyte from the first molecular analyte, the pH in the low pH step zone is further increased to a value intermediate between pH1 and pH 2, namely, to a point where pH(I)>pI1>pH(III)>pI2>pI3, for example as shown at FIG. 2D. Now, the second molecular analyte is negatively charge so as to drift towards the right end of the pH profile where it may be collected and/or diagnosed separately from the first and third molecular analytes. Finally, as shown at FIG. 2E, the pH value in the high pH step zone is increased to a value above pI1, and the first molecular analyte is negatively charged so as to drift toward the right end of the pH profile, where it may be collected or diagnosed separately from the third and the second molecular analytes. Clearly, any number of molecular analytes may be collected and/or diagnosed separately in this manner where the collection and/or diagnosis time may be temporally synchronized with the pI of the collected and/or diagnosed molecular analyte.

According to some embodiments of the present invention, the separation device 100 gradually changes the pH profile, for example increases the pH in one of the zones, for example the high pH step zone, monotonically with time, for example linearly. In such a manner, the molecular analytes are sequentially released, in a formation of separate drifting bands, which may be referred to as groups, as shown at FIG. 2E. The spatial separation between these bands may be made arbitrarily large by an arbitrarily slow increase in the pH of a certain zone, such as the low pH step zone, thus yielding an arbitrarily high resolution in pI separation between the bands. Optionally, the three bands may be collected as separate groups on the right end of a region corresponding with the right end of the pH profile by conventional fraction collectors and/or by other protein harvesting techniques. Additionally or alternatively, the three bands may be separately diagnosed on the right end of a region corresponding with the right end of the pH profile by conventional molecular probes and/or by other molecular probing techniques.

Figure 4A:
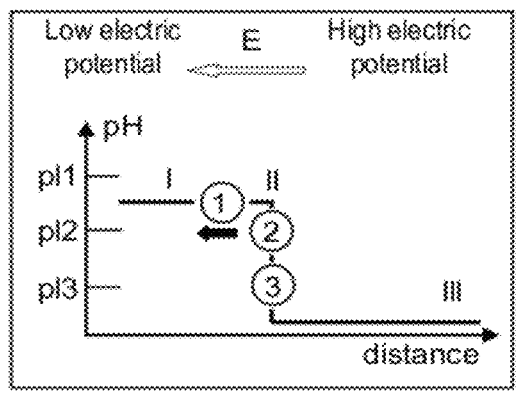
FIGS. 4A and 4B are schematic illustrations of a pH profile adjusted to induce the migration of molecular analytes to a direction which is opposite to the migration depicted in FIGS. 2A-2E, according to some embodiments of the present invention.
Figure 4B:
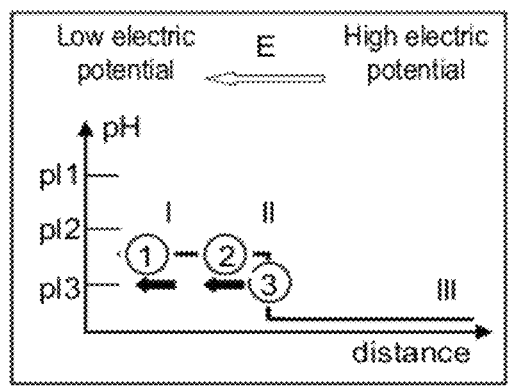

It should be noted that the pH profile may be adjusted, optionally gradually, to induce the migration of molecular analytes to the opposite direction by reducing the pH of one or more of the zones, for example as shown at FIGS. 4A and 4B. For example, the pH profile is adjusted to induce a migration of the molecular analytes, for example the first and second of the aforementioned molecular analytes by reducing the pH of zone I. In the depicted example, the pH profile is changed so that the pH in zone I is reduced to a value intermediate between pI1 and pI2, and then between pI2 and pI3 namely to a point where pI1>pH(I)>pI2>pI3>pH(III) and then pI1>pI2>pH(I)>pI3>pH(III).

Figure 4C:
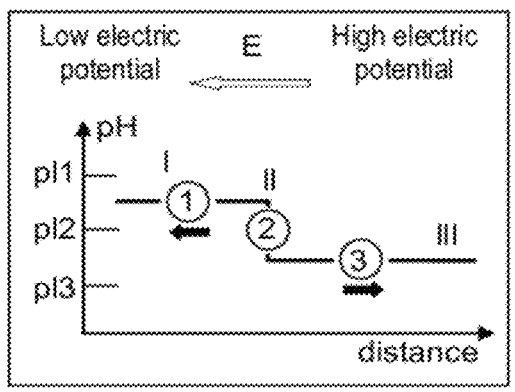
FIGS. 4C-4E are schematic illustrations of a pH profile adjusted to induce a bidirectional movement of molecular analytes, according to some embodiments of the present invention.

Optionally, as shown at FIG. 4C, the pH profile is changed to induce the migration of molecular analytes to two opposing directions. For example, the aforementioned pH profile depicted in FIG. 1A is adjusted to induce a migration of the molecular analytes to opposing directions, for example the first and third of the aforementioned molecular analytes, by reducing the pH of zone I and increasing the pH of zone III, simultaneously and/or gradually.

Figure 4D:
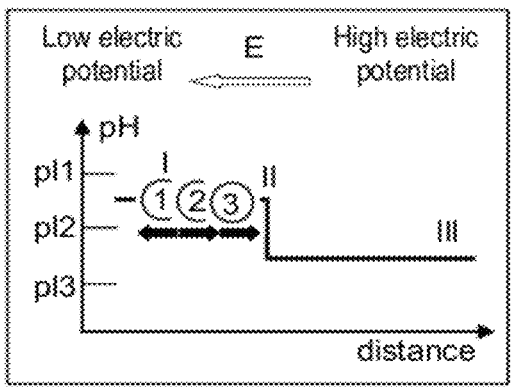

It should be noted that molecular analytes may be separated without being concentrated in a certain zone. For example, as shown in FIG. 4D, separation may occur in a pH step zone when the pH in this zone is different from the pI of molecular analytes therein. The separation is formed between a molecular analytes I and molecular analytes II and III as molecular analytes I is positive and molecular analytes II and III are negative and so migrate to different directions.

Figure 4E:
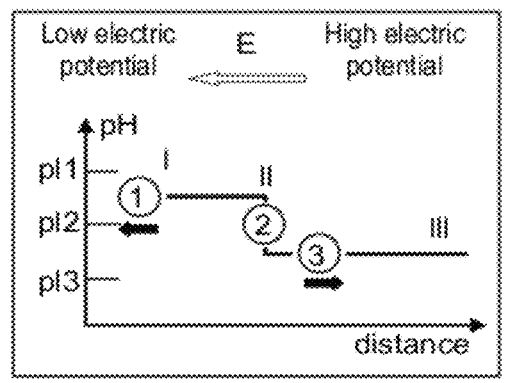

The same strategy may be applied to release, for example, the first molecular analyte to the left, the third molecular analyte to the right and capturing them in different pH ramps as depicted in FIG. 4E while holding the second molecular analyte in a middle pH ramp zone.

Figure 4G:
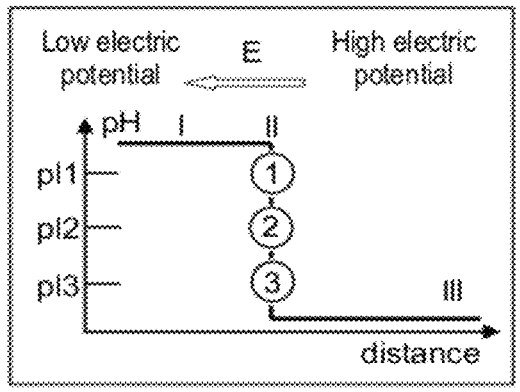
FIGS. 4G-4K are schematic graphical illustrations of a dynamic multistep pH profile and its effect on molecular analytes which are in the solution in a container over a period, according to some embodiments of the present invention.
Figure 4H:
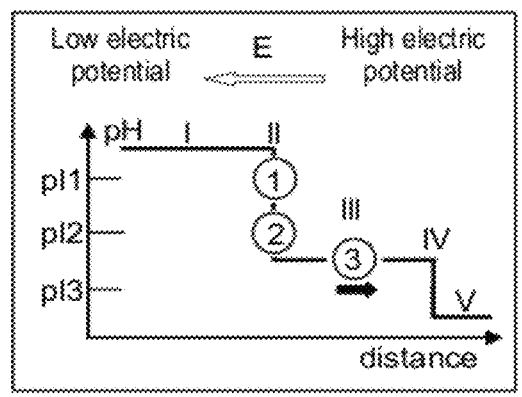
Figure 4I:
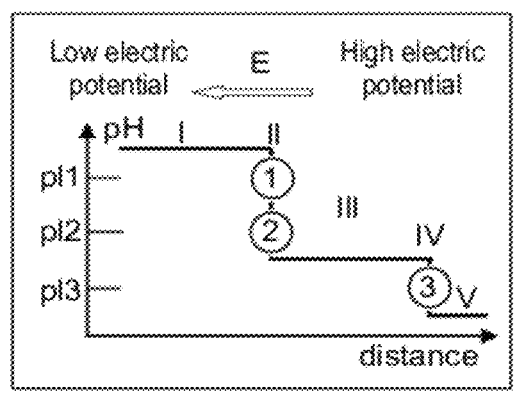
Figure 4J:
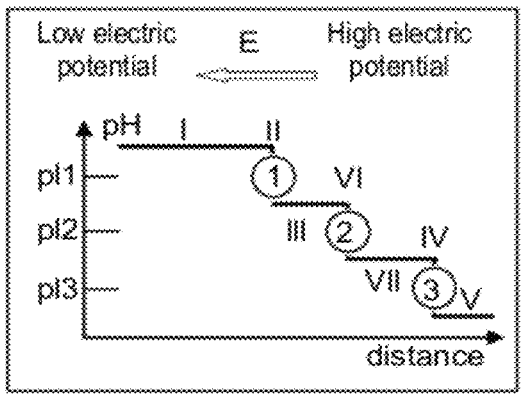
Figure 4K:
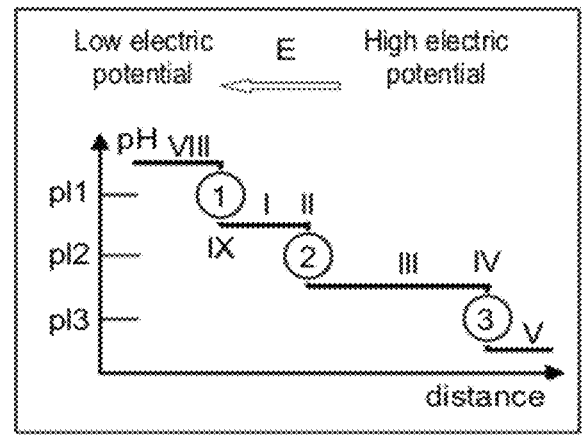
Figure 5A:
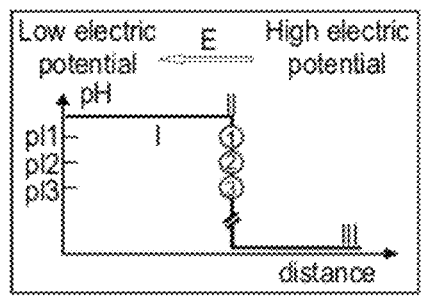
FIGS. 5A-5G are schematic illustrations that graphically depict how molecular analytes are sequentially drifted toward a pH ramp zone located in proximity to an end of the pH profile, according to some embodiments of the present invention.
Figure 5B:
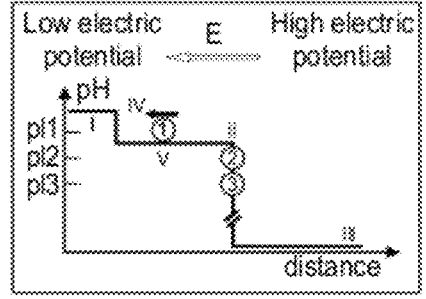
Figure 5C:
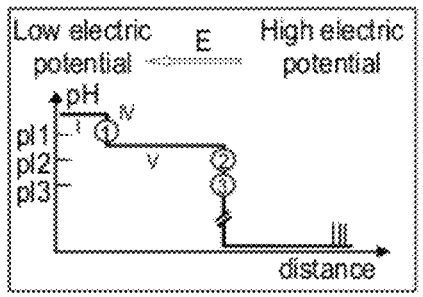
Figure 5D:
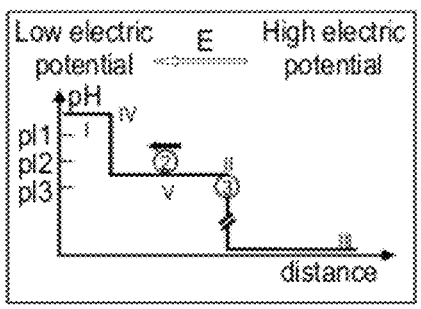
Figure 5E:
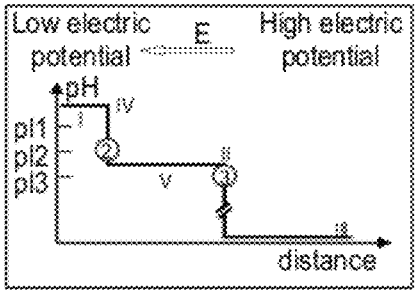
Figure 5F:
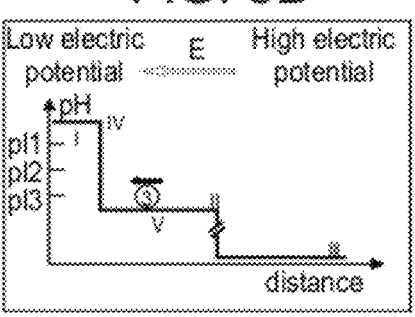
Figure 5G:
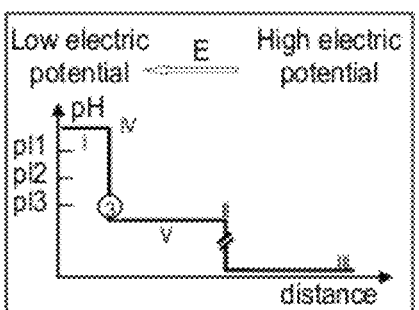

Reference is now made to FIGS. 4G-4K which are schematic graphical illustrations of a dynamic multistep pH profiles and their effect on molecular analytes which are in the solution in a container over a period, according to some embodiments of the present invention. In the depicted embodiment, a number of pH ramp zones are formed between different pH step zones sequentially arranged based on their pH. This allows harvesting and/or diagnosing molecular analytes with different pIs from and/or in different location along the pH profile axis. Such a multistep pH profile allows forming well defined protein bands which are amenable for harvesting by conventional protein band harvesting methods. FIG. 4G is identical to FIG. 2A, which satisfies pH(I) >pI1>pI2>pI3>pH(III). In FIG. 4H, the low pH step zone, marked as zone III, is increased to a value intermediate between pI3 and pI2, namely to a point where, pH(I) >pI1>pI2>pH(III)>pI3. An additional pH ramp zone, denoted as IV, and another pH step zone, denoted as V, are formed to the right of zone III, as shown at FIG. 4H such that pI3>pH(V). Under such a pH pattern, pH(I)>pI1>pI2>pH(III)>pI3>pH(V) and the third molecular analyte is negatively charged so as to drift toward the right end and being trapped in pH ramp IV, as shown at FIG. 4I. The first and second molecular analytes remains trapped in pH ramp zone II. Upon further pH increase in pH step zone III, to a point where pH(I)>pI1>pH(III)>pI2>pI3, and a formation of a third pH ramp zone and a third pH step zone, marked as VI and VII, respectively, in FIG. 2J such that pH(I)>pI1>pH(III)>pI2>pH(VII)>pI3>pH(V). The second molecular analyte is released from the trap and drifts toward the right end until being captured in pH ramp zone VI. Each one of the three molecular analytes are now captured in different pH ramp zones, as shown at FIG. 4K and may be diagnosed and/or harvested directly and/or released, optionally separately at different times, to be collected at the right edge.

In such embodiments, the separation performed by simply injecting ions into the channel according to a certain pattern. This allows focusing molecular analytes, such as proteins, in a number of places along the channel, each in a pH ramp zone. The focusing is performed before separately collecting and/or diagnosing the molecular analytes. In such a manner, the yield may be increased and different proteins may be focused in different preset locations, time after time, so that a harvesting unit may harvest in fixed locations.

It should be noted that the inducing of migration of molecular analytes toward the left end of the pH profile may be similarly performed when the pH of one or more zones are reduced. For example, FIGS. 5A-5G depict how molecular analytes such as different proteins are sequentially drifted toward a ramp located in proximity to the left end of the pH profile. The gradual drifting depicted in these figures is performed by reducing the pH in pH step zone V. This allows sequentially and separately collecting and/or diagnosing the molecular analytes.

Figure 6:
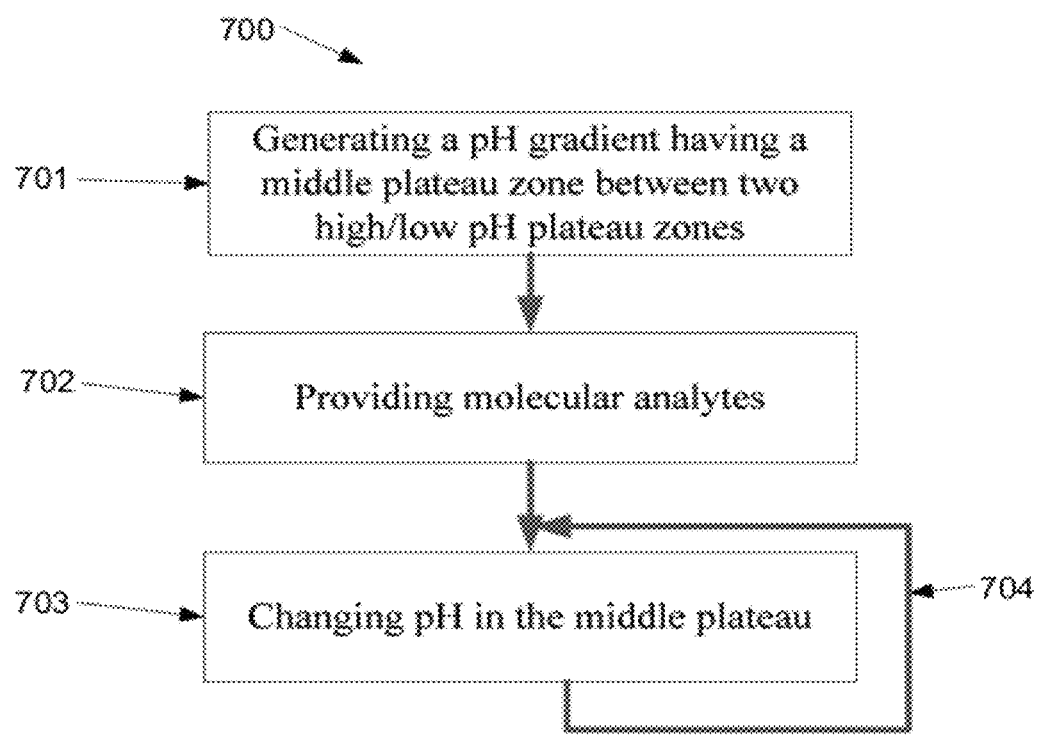
FIG. 6 is a method of separately drifting molecular analytes having different pIs in relatively high velocity along a pH profile, according to some embodiments of the present invention.
Figure 7A:
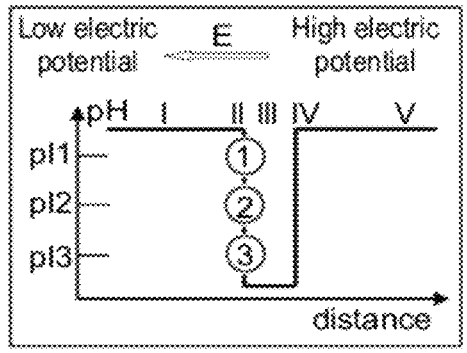
FIGS. 7A-7E are schematic illustrations that graphically depict how molecular analytes are drifted in relatively high velocity along a dynamic pH profile, according to some embodiments of the present invention.
Figure 8A:
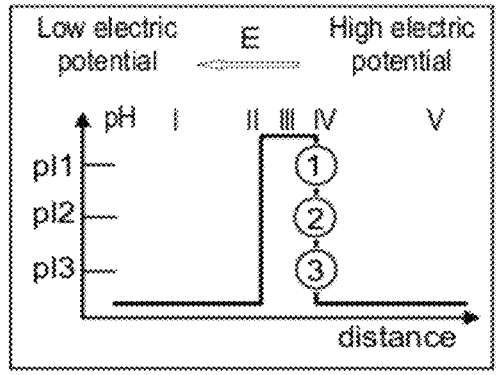
FIGS. 8A-8E are additional schematic illustrations that graphically depict how molecular analytes are drifted in relatively high velocity along a dynamic pH profile, according to some embodiments of the present invention.
Figure 8B:
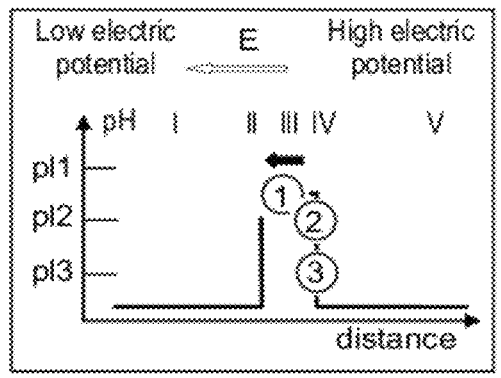

Reference is now made to FIG. 6, which is a method 700 of separately drifting molecular analytes having different pIs in relatively high velocity along a pH profile, according to some embodiments of the present invention. As described above, the molecular analytes drift along the pH profile axis until they reach a zone in which they do not carry a net electrical charge. The drift velocity of each molecular analyte is proportional to its charge that is a derivative of the pH in the hosting zone in the solution. First, as shown at 701, a pH profile with a middle step zone between two high/low pH step zones is formed. The pH profile may include two high pH step zones separated by a low middle pH step zone or a pH profile with two low pH step zones separated by a high middle pH step zone. For brevity, pH profiles with such profiles are respectively referred to herein as a high-low-high pH profile and a low-high-low pH profile. FIG. 7A and FIG. 8A respectively depict such profiles for three exemplary molecular analytes.

Now, as shown at 702, molecular analytes are provided from one side of the pH profile axis, for example one side of the container 102, for instance the left side, depends on the pattern of the pH profile. The injection is performed so as to trap the molecular analytes in a pH ramp zone. If the profile is high-low-high than the molecular analytes may be injected to the channel from anywhere except the high step zone on the high potential side, for example, in FIG. 7, the right side. Otherwise, the molecular analytes may not focus. In this case the molecular analytes focus on the ramp located on the lower potential side, for example as depicted in the left side of FIG. 7. Alternatively, if the profile is low-high-low than the analytes may be injected to the channel from anywhere except the low step zone on the low potential side, for example as depicted in the left side of FIG. 8. In this case the molecular analytes focus on the ramp located on the higher potential side, for example as depicted in the right side of FIG. 8. The molecular analytes drift until being trapped in a pH ramp zone between the high and low step zones, for example as shown at FIGS. 7A and 8A. As described above, trapped molecular analytes are trapped when attempts to drift to one side are instilled by a negative charge that pushes the molecular analytes back to the trapping zone and attempts to drift to another side are instilled by a positive charge that similarly pushes the molecular analytes back to the trapping zone.

Initially, as depicted in FIG. 7A, the profile is defined so that pH(I)=pH(V)>pI1>pI2>pI3>pH(III) and three exemplary molecular analytes, such as proteins, are captured in pH ramp zone II. The step zone III is made as short as possible, preferably in the range of between about 10 micrometers and 1000 micrometers, to minimize the protein traveling time in zone III where their charge is relatively small.

Figure 7B:
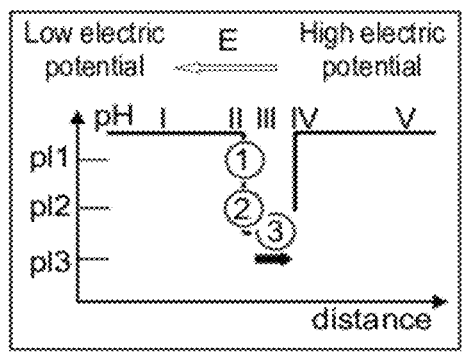
Figure 7C:
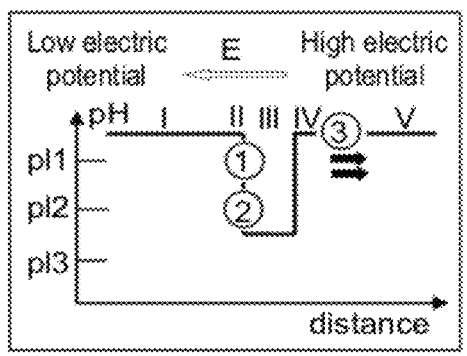
Figure 7D:
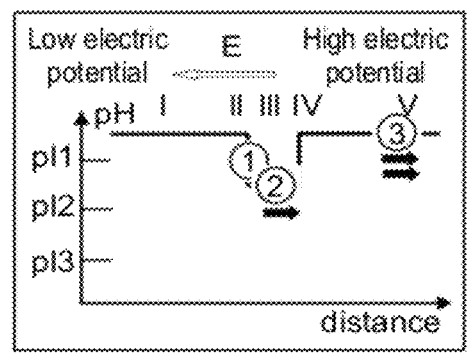
Figure 7E:
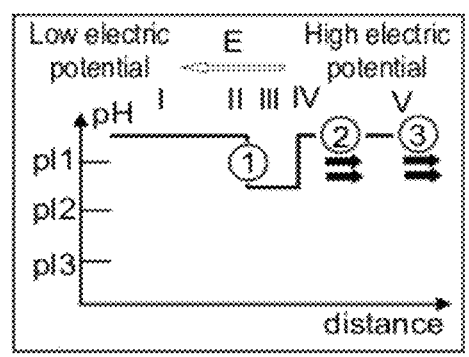
Figure 8C:
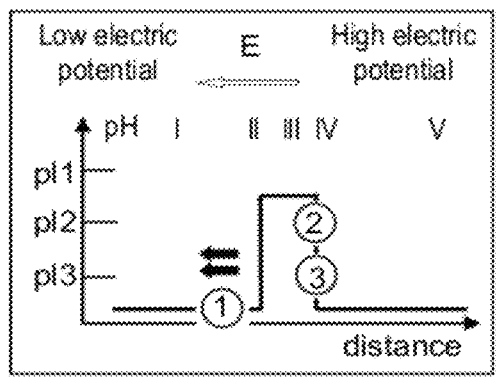
Figure 8D:
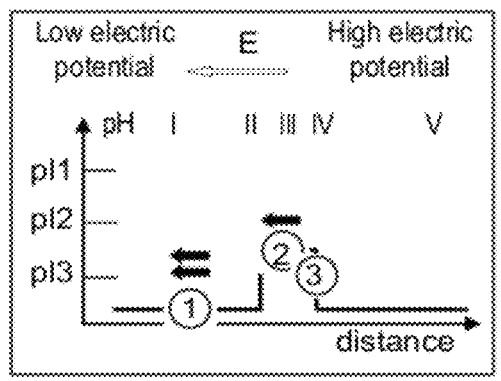
Figure 8E:
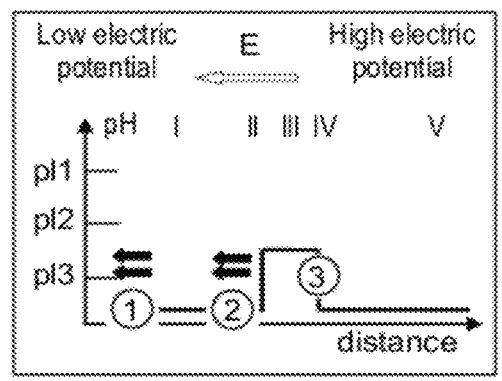

Now, as shown at 703, the middle step zone of the pH profile is adjusted to induce the migration of one or more of the trapped molecular analytes. For example, FIG. 7B depicts the adjusting of the pH profile to induce the migration of the third molecular analyte, marked as pI3, by increasing the pH of the middle plateau to a point where pH(I)=pH(V) >pI1>pI2>pH(III)>pI3. This increment releases the third molecular analyte from pH ramp zone II, as before, while the other molecular analytes remain trapped. The slightly negatively charged third molecular analyte drifts to the right end until hitting pH ramp zone IV. At that point, the pH, and hence the negative charge of the third molecular analyte, grows dramatically. Consequently, the third molecular analyte drift velocity is dramatically accelerated, for example 10 times, 100 times or 1000 times faster, as shown at FIG. 7C shortening the separation time in relation to a separation according to the method depicted in FIG. 1. For brevity, a higher velocity is marked by double arrow. As shown at 704, the profile may be adjusted in a plurality of stages so as to release the molecular analytes in a sequential manner. For example, the pH at the middle pH step zone is increased and/or reduced in a sequential manner, for example as shown at FIGS. 7A-7E and FIGS. 8A-8E. In FIGS. 8A-8E, the separation is performed from in a descending pI order. The starting pH profile for three exemplary molecular analytes is pH(III)>pI1>pI2>pI3>pH(I)=pH(V), and the three molecular analytes trapped in pH ramp IV are depicted in FIG. 8A. In use, the pH of pH step zone III is slowly lowered as a function of time to a point where pI1>pH(III)>pI2>pI3>pH(I)=pH(V). In this regime, the first molecular analyte is charged positively and starts drifting to the left. Upon hitting pH ramp II the pH drops and the positive charge of the first molecular analyte and its drift velocity increases dramatically, for example as shown at FIG. 8C. The same process is sequentially repeated with the second and third repeated molecular analytes, as shown at FIGS. 8D and 8E.

Figure 9A:
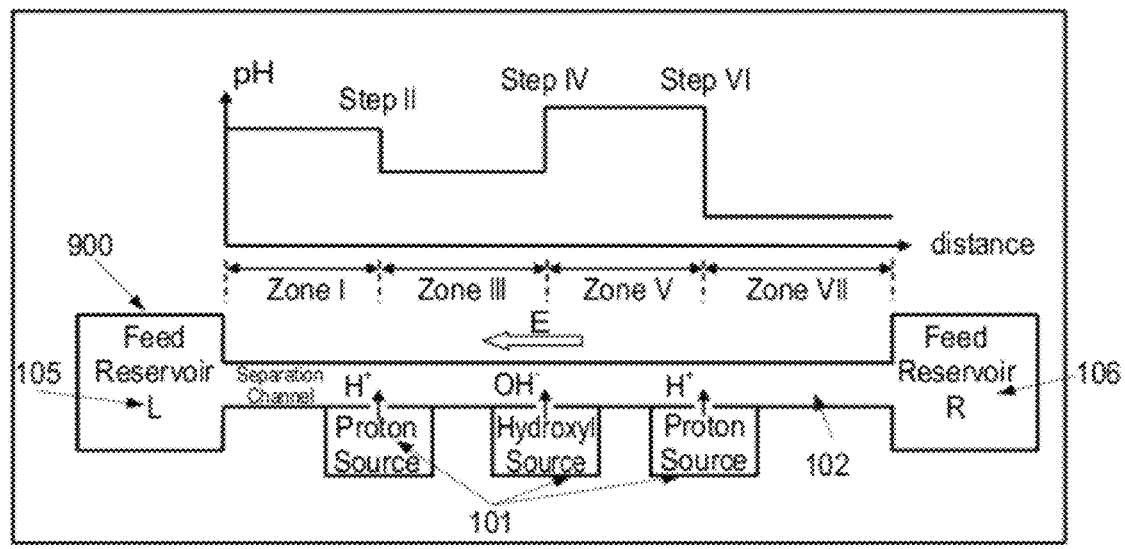
FIG. 9A is a schematic illustration of an exemplary device of separating molecular analytes based on their pI, according to some embodiments of the present invention.

Reference is now made to FIG. 9A, which is a schematic illustration of an exemplary device 900 of separating molecular analytes based on their pI, for collecting and/or diagnosing a mixture having one or more molecular analytes, according to some embodiments of the present invention. FIG. 9A further depicts a schematic plot of a pH profile that is generated in the container 102 of the exemplary device 900.

The exemplary device of 900 is as depicted in FIG. 3A, however, the ion sources 101 are based on ion injection, as further described below. The container 102 with a proper electrolyte solution that defines a confined separation volume in which the pH profile is generated and adjusted, for example as described above. An electric field traverses the separation volume, for example as described above. The ion sources 101 are set to inject protons and/or hydroxyl ions in a controlled manner to specific zones along the pH profile axis that is formed in the separation volume. The container includes means for introducing a mixture of molecular analytes, such as proteins and harvesting the products of the separation process.

Figure 9B:
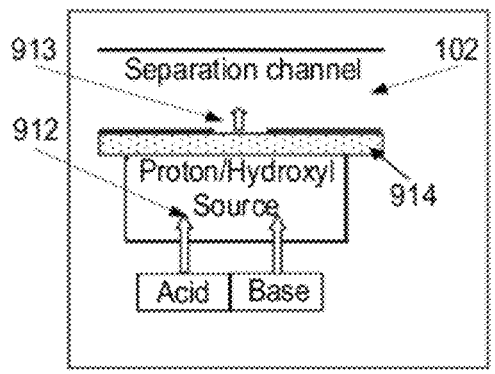
FIGS. 9B-9D are schematic illustrations of exemplary ion sources that may be used in the exemplary device of FIG. 9A, according to some embodiments of the present invention.
Figure 9C:
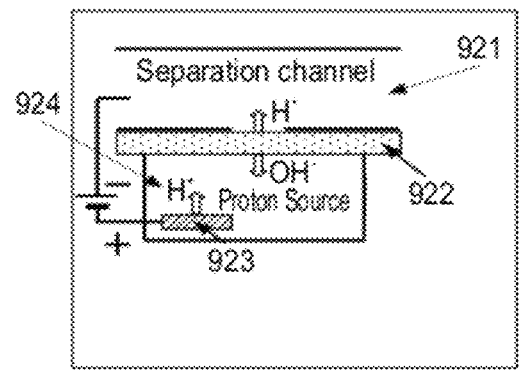
Figure 9D:
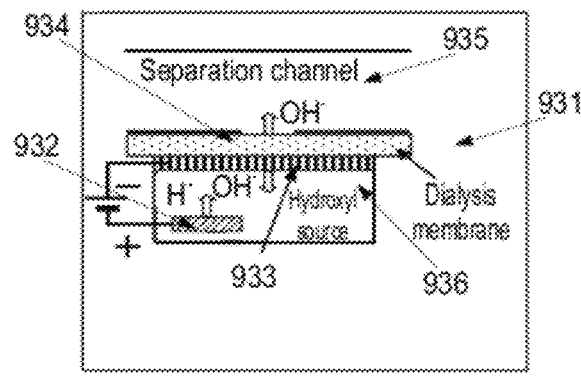

In the depicted embodiment, the container 102 of the device defines the separation in an elongated channel fed by two reservoirs. The channel 102 length may vary from a few tens of microns, if fabricated by micromachining technology, to a few millimeters, centimeters, or tens of centimeters if fabricated by conventional methods. The channel average diameter and thickness may vary between one micrometer and a few centimeters, for example between one micrometer and/or one millimeter in width. The proton and hydroxyl ion sources 101 are distributed along the channel and set to inject ions into zones in the channel. For example, three hydroxyl sources and two proton sources are respectively used to form the pH profiles depicted in FIG. 4 and FIG. 5. Examples for such ion sources are depicted in FIGS. 9B-9D which are schematic illustrations of various exemplary ion sources that may be used, simultaneously or interchangeably in the exemplary device of 900, according to some embodiments of the present invention. FIG. 9B depicts a proton/hydroxyl source 911 that includes a small chamber 912 coupled to the separation channel 102 through an opening 913 and a dialysis membrane 914. The dialysis membrane prevents or reduces protein leakage from the separation channel 102 to the small chamber 912 while permitting ion exchange between these volumes. The proton/hydroxyl source 911 set the pH in a proximate zone in the separation volume by mixing acid and base solutions in the chamber 912. For example, if the ion source is a proton source, excess acid solution is mixed with a base solution to give a zone having an overall pH<7. If the ion source is a hydroxyl source, the opposite is held and pH>7 is formed in the zone. Optionally, the acid and base solutions are placed in separate vessels fed to the corresponding proton/hydroxyl source chamber in desired amounts.

FIG. 9C depicts an electrolysis based ion source 921 that generates protons by splitting water using a bipolar membrane 922 and a voltage applied across the membrane between the separation channel 102 and a platinum electrode 923 immersed in a proton source chamber 924. Optionally, the electrolysis based ion source 921 is as defined in Provisional Patent Application No. 61/272,110 filed on Aug. 18, 2009, which is incorporated herein by reference. The polarity of the bipolar membrane 922 is chosen such that protons are generated on the channel side of the membrane 922 while hydroxyl ions are generated on the chamber side. The bias applied to the membrane 922 is chosen such that the negative terminal is fed to the channel side of the membrane while the positive terminal is fed to the platinum electrode. Under these conditions water splits in the membrane. The generated protons are injected into the channel and the hydroxyl ions are injected from the membrane into the chamber where they recombine with protons generated on the platinum electrode 923 to produce water. Clearly, and as described in Provisional Patent Application No. 61/272,110, a hydroxyl ion source may be similarly constructed. To that end, a bipolar membrane is flipped together with the polarity of a voltage source. In this configuration the hydroxyl ions generated by water splitting in the membrane 922 are injected into the separation channel while the protons are injected into the hydroxyl source chamber 924 where they recombine with hydroxyl ions generated on the platinum electrode to give water.

FIG. 9D depicts another ion source 931 were water is electrolyzed by applying voltage between two platinum electrodes 932, 933 immersed in a source chamber 936. The platinum electrode 933 next to the channel 935 may be perforated to improve ion transport to the channel. In the case where the cathode electrode is closer to the separation channel, hydroxyl ions are injected into the channel. To inject protons into the channel the bias polarity is reversed so that the anode is now adjacent to the channel.

Reference is now made to a description of a method of forming and adjusting a pH profile for inducing the migration of molecular analytes along the axis of the pH profile. The method is performed by injecting protons and/or hydroxyl ions into a channel supporting an electric field, which is harnessed to the generation of a pH profile, such as container 102. The description herein also teaches an appropriate electrolyte and injection currents selection for achieving the desired pH profile in space and optionally the changing thereof in time. A simple approximation to the full computation is disclosed herein as an algorithm for a simulator of a device operation for the design of separation processes by the device described above in relation to FIG. 9A.

A pH distribution across a separation volume in a channel, such as 102, may be described by the following transport equations for all ions involved:

$$\partial C_i / \partial t + \vec{\nabla} \cdot (-D_i \vec{\nabla} C_i + z_i F \mu_i C_i \vec{E}) = R_i \qquad \text{Equation 1:}$$

coupled with the following Poisson-Boltzmann equation:

$$\vec{\nabla} \cdot \vec{E} = 1.4 \times 10^{14} \cdot \sum_i z_i C_i. \qquad \text{Equation 2}$$

at the right boundary and starting conditions. In meter, kilogram, and/or second (MKS) units, $C_i$ denotes a molar concentration of ion of specie i, $D_i$ denotes the diffusion coefficient of i, $\mu_i$ denotes the electrical mobility of i, $z_i$ denotes a charge in proton charge units of i, F denotes the Faraday constant, $R_i$ denotes the reaction terms of specie i, and $\vec{E}$ denotes the electric field in the focusing channel, such as of container 102. It should be noted that although the examples herein are described with relation to protein, any molecular analyte may be used.

Optionally, the latter equations take into account chemical reactions that take place in the solution so as to form a set of several non-linear differential equations that allows computing a numerical solution.

Optionally, the following allows programming of a pH profile generator that generates a dynamic pH profile for the aforementioned separation process. Taking advantage of the fact that the chemical reactions, such as proton-hydroxyl recombination, are relatively fast and the fact that ion drift in the external electric field dominates over certain ion diffusion, except for immediate vicinity of proton/hydroxyl injection, an analytically tractable model that captures the essential physical phenomena in steady state may be formulated. The model elucidates the modus operandi of the aforementioned devices during the separation process and provides a tool for selecting parameters for generating a desired pH profile. The simplified model hence discloses an algorithm for a simulator useful in the planning of molecular analytes separation assays, such as protein assays, for the device.

For brevity, two types of pH change operations are defined, a focusing pH ramp and a defocusing pH ramp. A focusing pH ramp is characterized by a higher pH value at the low electric potential side of the pH ramp and a lower pH value at the high electric potential side of the pH ramp, for example as depicted in FIG. 2A. A defocusing pH ramp is opposite, namely characterized by a lower pH value at the low electric potential side of the pH ramp and a higher pH value on the high electric potential side of the pH ramp, for example pH ramp IV depicted FIG. 7A. A focusing pH ramp captures all proteins having a pI between the high and low pH values of the pH ramp. A defocusing pH ramp does not capture proteins for extended periods of time.

Figure 10A:
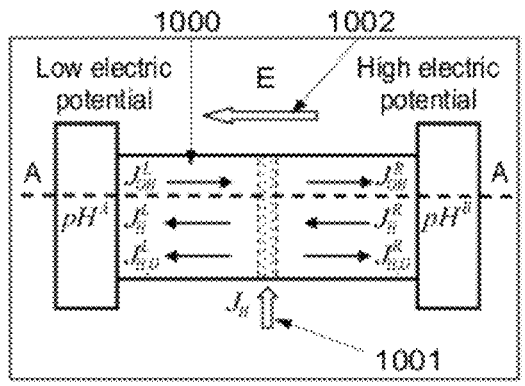
FIG. 10A and FIG. 10E depict a container, such as depicted in FIG. 3, having a non buffered solution, together with the relevant current densities, in the cases of proton and hydroxyl injections, according to some embodiments of the present invention.
Figure 10E:
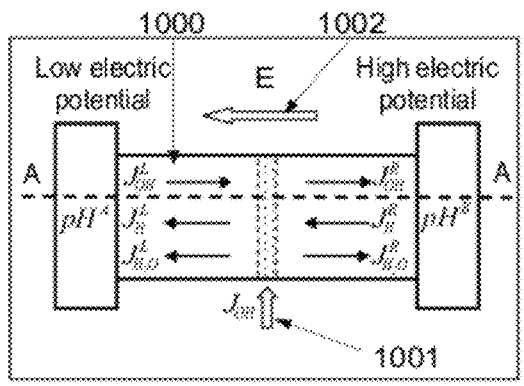
Figure 10B:
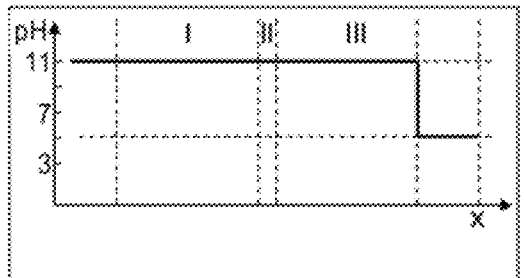

According to some embodiments of the present invention, the pH profile is formed in a saline solution carrying no buffer molecules. FIG. 10A and FIG. 10E depict proton and hydroxyl injection into a separation channel 1000 such as of the aforementioned devices 100, 900, respectively. The separation channel 1000, which is fed by left and right reservoirs, is characterized by two pH values, respectively denoted herein as $pH^A$ and $pH^B$, where $pH^A > pH^B$. Relevant ionic (particle) current densities in the channel are depicted together with an injection current 1001 into the channel 1000, and a direction of the electric field 1002. FIGS. 10B-10D and FIGS. 10E-10H depict an exemplary pH profile along a pH profile axis under various injection conditions. The pH profile axis is marked as a dashed A-A line in FIGS. 10A and 10E. In FIGS. 10B-10D, $pH^A=11$ and $pH^B=5$. FIG. 10B depicts the pH profile in the absence of injection current where $J_H=0$. The hydroxyl current fed by the left reservoir dominates over the proton current fed by the right reservoir and the proton-hydroxyl recombination front stabilizes at the interface between the separation channel and the right reservoir. The pH throughout the channel is identical to the pH in the left reservoir.

FIG. 10C depicts the pH profile after some protons were injected into the channel. The pH to the right of the injection point at pH step zone III is reduced, as shown by the solid line in FIG. 10C, to form a focusing pH ramp. For an increased proton injection, the focusing pH ramp is steepening until it reaches its maximal value, for example marked by a dashed-dotted line in FIG. 10C. Increasing the injection beyond this limiting value of ion current, would result in pH ramp turn-over, transforming it from a focusing pH ramp to a defocusing pH ramp. The result is shown in FIG. 10D. It should be mentioned that in a focusing pH ramp, the pH of zone I remains while the pH of zone III varies according to current. The opposite holds in a defocusing pH ramp, namely, the pH in zone III stays constant while its corresponding value in zone I varies according to the applied current.

For example, when a dynamic pH profile as depicted in FIG. 2A is generated, the resulting dashed-dotted focusing pH ramp of FIG. 10C focuses all proteins having a pI between pH 11 and pH 7. When the proton injection current is reduced to create the pH ramp depicted by the solid line of FIG. 10C, all proteins having a pI between pH 7 and pH 9 are released. In relation to FIG. 7A, the defocusing pH ramp depicted in FIG. 10D may accelerate the rightwards migration of proteins, having pI<3. Defocusing pH ramps, created at excessive proton injections, may be utilized to implement the dynamic pH profile depicted in FIGS. 7A-7E where both focusing and defocusing pH ramps are required.

Figure 10F:
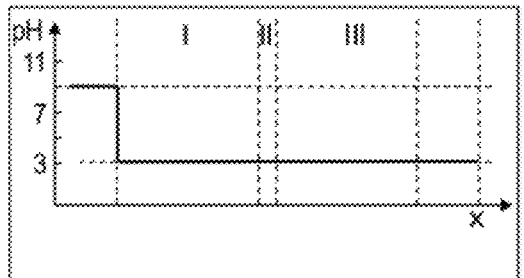
Figure 10C:
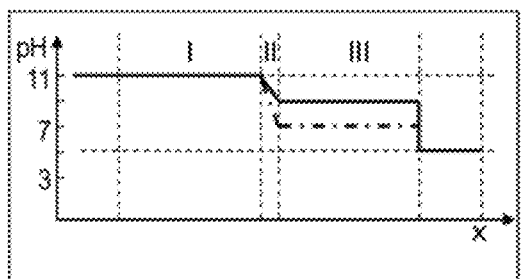
Figure 10G:
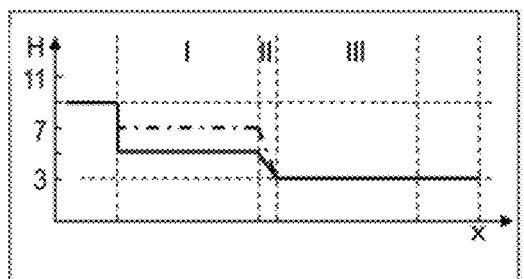
Figure 10D:
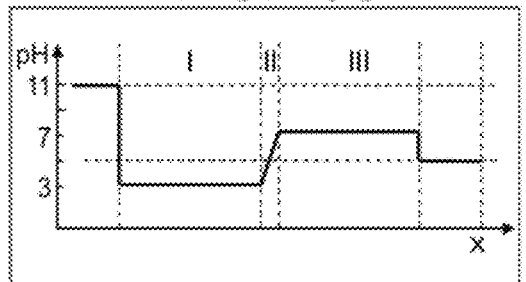
Figure 10H:
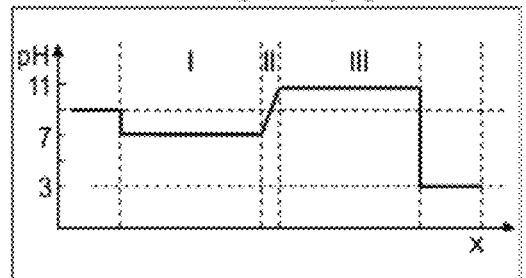

FIG. 10F depicts the pH profile for the case where $pH^A=9$, $pH^B=3$ and $J_{OH}=0$. Since the proton current, which is fed by the right reservoir, dominates over the hydroxyl current fed by the left reservoir, the pH in the channel 102 is equal to $pH^B$. In FIG. 10G, similarly to the depicted in FIG. 10C, small injection of hydroxyl ions create the focusing pH ramp depicted by the solid line, while the dashed dotted line illustrates the maximal focusing pH ramp achieved when the limiting current is applied. Exceeding this current would cause the pH ramp to flip, as depicted in FIG. 10H. The sequence depicted in FIGS. 4A-4E may be realized in this configuration for proteins having an isoelectric point between pH 3 and pH 7. The steady state pH value in zones I and III of FIGS. 10A-10D may be computed using the following equation:

$$J_{OH}^I - J_{H_2O}^I = J_{H_2O}^{III} + J_{OH}^{III}; \text{ and} \qquad \text{Equation 3:}$$

$$J_H^I + J_{H_2O}^I = J_H + J_H^{III} - J_{H_2O}^{III}. \qquad \text{Equation 4:}$$

And for the case of hydroxyl ion injection, as depicted FIGS. 10E-10H, the equations are:

$$J_{OH}^I + J_{OH} - J_{H_2O}^I = J_{H_2O}^{III} + J_{OH}^{III} \qquad \text{Equation 5:}$$

$$J_H^I + J_{H_2O}^I = J_H^{III} - J_{H_2O}^{III}. \qquad \text{Equation 6:}$$

Equations 3 and 5 express hydroxyl ions conservation and Equations 4 and 6 express the proton current conservation. The two equations take into account water generation and decomposition by the following reaction $$H^+ + OH^- \leftrightarrow H_2O, \qquad \text{Equation 7:}$$

with the corresponding law of mass action $$[H^+]^{I,III}[OH^-]^{I,III} = K_W. \qquad \text{Equation 8:}$$

where $J_H^{I,III}$, $J_{OH}^{I,III}$, $J_{H_2O}^{I,III}$ respectively denotes proton, hydroxyl and water particle current densities in zone I and III, $[H^+]^{I,III}, [OH^-]^{I,III}$ respectively denotes molar concentrations of protons and hydroxyl ions in the respective zones, and $K_W = 10^{-14} M^{-2}$ denotes water equilibrium constant.

Under these exemplary conditions ions which drift caused by electric field dominate over drift cause by diffusion, the current densities are simply proportional to the following ion densities

$$J_H^{I,III} = v_H[H^+]^{I,III}; J_{OH}^{I,III} = v_{OH}[OH^-]^{I,III}. \qquad \text{Equation 9:}$$

Solving equations 3, 4, 8 and 9 for proton injection and/or 5, 6, 8, and 9, for hydroxyl injection, render the parameters needed for generating a dynamic pH profile for inducing molecular analytes migration and focusing along the pH profile. The relations between ion concentrations in zones I and III may be obtained by allowing calculations of focusing or defocusing pH ramp sizes as a function of the injected ions. In addition, the model predicts the value of maximal attainable pH focusing ramp before pH ramp turnover, together with its corresponding limiting current. Note that the set of equations to be solved are algebraic rather than partial differential equations, hence, a rapid calculation of the resulting pH ramp is facilitated in a short time, using a relatively modest computing power.

According to some embodiments of the present invention, the pH profile is formed in a buffered solution, such as a saline solution carrying buffer molecules.

The two buffer species denoted herein as $AH^-$ and $A^{-2}$ and participate in the reaction:

$$H^+ + A^{-2} \Leftrightarrow AH^- \quad \text{Equation 10}$$

with the following equilibrium constant Ka:

$$Ka = \frac{[A^{-2}]\cdot[H^+]}{[AH^-]} \quad \text{Equation 11}$$

In the case of proton injection, the mass balances for the protons, hydroxyl ions, and the buffer molecules may be defined as follows:

$$J_{OH}^I - J_{H_2O}^I = J_{H_2O}^{III} + J_{OH}^{III}, \quad \text{Equation 3}$$

$$-J_{AH}^I + J_H^I + J_{H_2O}^I = J_H + J_H^{III} - J_{H_2O}^{III} - J_{AH}^{III}, \quad \text{Equation 12}$$

$$J_A^I + J_{AH}^I = J_A^{III} + J_{AH}^{III}. \quad \text{Equation 13}$$

where $J_{AH}^{I,III}$ and $J_A^{I,III}$ denote current densities of the two buffer forms. The mass balance for hydroxyl ions, as defined in Equation 3, stays the same, while that of protons, as defined Equation 12 is modified to account for the protons carried by the buffer molecules. Equation 13 defines a mass balance for buffer molecules. As in the case of protons and hydroxyl ions, set in Equation 9, the current of these species are proportional to their concentrations, $$J_{AH}^{I,III} = v_{AH}\cdot[AH^-]^{I,III},$$

$$J_A^{I,III} = v_A\cdot[A^{-2}]^{I,III}, \quad \text{Equation 14:}$$

If hydroxyl ions rather than protons are injected, $J_H$ should be removed from equation 12, and $J_{OH}$ should be added on the left hand side of Equation 3.

Solving Equations 3, 8-9, and 11-14 renders the relations between the species concentrations in each zone, and enables the calculation of pH ramp steepness, maximal pH focusing ramp, and corresponding limiting currents.

Figures 11A, 11C:
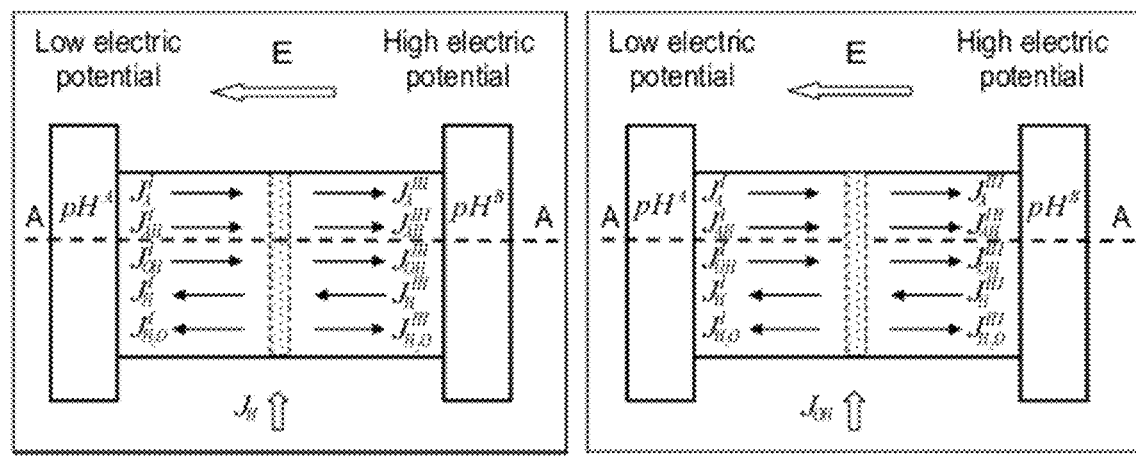
FIG. 11A and FIG. 11C depict a container, such as depicted in FIG. 3, having a buffered solution, together with the relevant current densities, in the cases of proton and hydroxyl injections, according to some embodiments of the present invention.
Figures 11B, 11D:
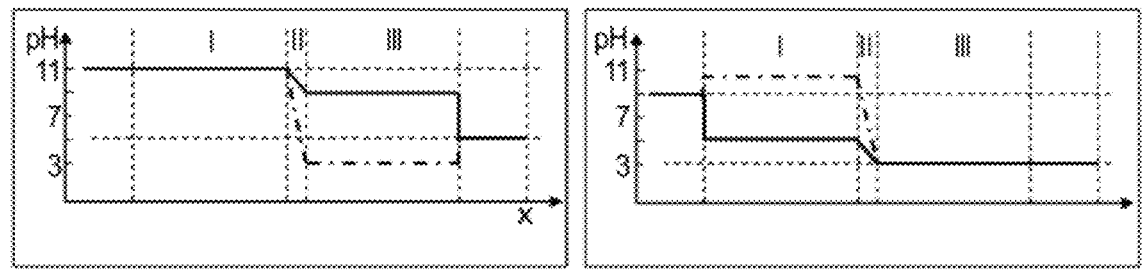
FIG. 11B and FIG. 11D depict a pH profile along an axis, such as depicted in FIG. 11A and FIG. 11C, according to some embodiments of the present invention.
Figure 12:
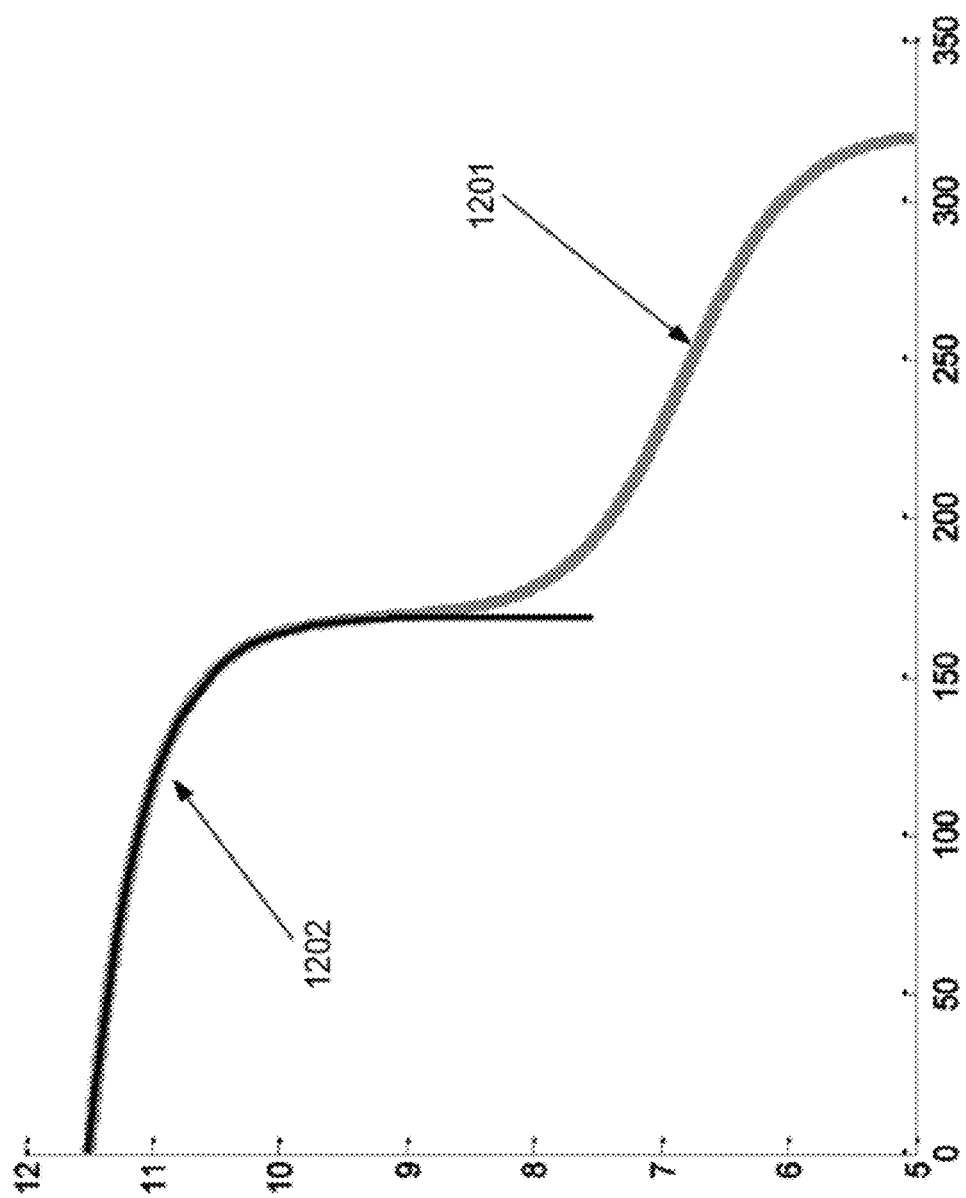
FIG. 12 is a graph depicting the correlation between change in the electric current and the pH of a buffered solution and a non buffered solution, according to some embodiments of the present invention.

Reference is made to FIG. 11A and FIG. 11C which depict a container, such as 102, having a buffered solution, together with the relevant current densities, in the cases of proton and hydroxyl injections, respectively. As in the case of FIG. 11A and FIG. 11B, the pH levels in the reservoirs are $pH^A=11$ and $pH^B=5$ when protons are injected, and $pH^A=9$ and $pH^B=3$ when hydroxyl ions are injected. Reference is also made to FIG. 11B and FIG. 11D which depict a pH profile along an axis, such as the dashed A-A line in FIG. 11A and FIG. 11C. As before, the solid line in FIG. 11B and FIG. 11D presents a focusing pH ramp created by applying a small injection current, while the dashed-dotted lines present a largest focusing pH ramp attainable when the limiting current density is applied. Similarly to the described above, the raising of the current above its limiting value results in pH ramp turnover. By comparing between FIG. 11B and FIG. 10C, and between FIG. 11D and FIG. 10G it is apparent that the maximal focusing pH ramp in the presence of buffer molecules, are larger than their corresponding ones when buffer molecules are absent. In the specific example of proton injection, shown in FIG. 11B, a suitable amount of buffer is added to enable a maximum focusing pH ramp size that reaches an acidic pH to a value below that of the right reservoir. This stands in contrast to FIG. 11C, which demonstrates that a maximal focusing pH ramp in a non buffered solution reaches down only to a neutral pH. FIG. 12, which is a graph depicting the correlation between change in the electric current and the pH of a buffered solution and a non buffered solution in zone III when protons are injected, further stresses this point as it presents the difference between two pH plots at initial pH of 11.5 and an ending pH at its limiting current. One for a buffered solution 1201, where pKa=7 and $A_{TOT}=A^{-2}+AH^-=10$ mM), and the other for a non buffered solution 1202. As depicted in FIG. 12, the limiting current of the buffered solution 1201 is much higher than that of the non buffered solution 1202. Furthermore, the minimum pH level in the former is much lower than that in the latter. A closer inspection of the figure reveals that between pH 11.5 and pH 9, the two solutions behave basically the same. This is because in this range the only species reacting with the protons are the hydroxyl ions. Beyond this point, the non buffered system breaks down quickly, for example converts to a defocusing ramp, while the buffered solution continues to maintain a stable focusing pH ramp through the consumption of $A^-$ molecules. This feature, demonstrated also in FIG. 11B, indicates that in a buffered solution, larger focusing pH ramp may be generated. In the absence of buffer, the focusing pH cannot be reduced beyond pH≈7, while In the presence of an appropriate buffer, the range may be extended to acidic regimes, down to pH≈4 and even below, enabling implementation pH profiles in larger pH ranges. It should be mentioned that the extension of pH step sizes can be made also in the basic regimes when hydroxyl ions are injected. For example, as depicted in FIG. 11C, the pH step size in the presence of appropriate buffer, can reach basic pH's as high as pH≈10 and even beyond. As indicated in FIG. 12, a high resistivity to current is reached at pH 7 which equals to the buffer's logarithmic acid dissociation constant (pKa). This suggests that a stable focusing pH ramp may be created using a buffer whose pKa is close to either to $pH^I$ or $pH^{III}$.

Optionally, the buffered solution is adjusted to obtain a selected range of currents to be applied to the system. For example, the container 102 is a channel with a typical cross section of 1 mm and filled with a non-buffered solution of pH 8. A non buffered solution in which the proton concentration raises to pH 7 requires a current of approximately ≈4·10$^{-8}$ A, which is extremely difficult to apply. Furthermore, the stability of the ramp in this case would be very low as any small deviation from this exact current would result in a strong deviation in pH. If, however a 10 mM buffer of pKa=7, is added, the necessary current for creating such a ramp increases to ≈5·10$^{-5}$ A, a far more feasible current with much higher stability against fluctuations.

According to some embodiments of the present invention, the pH profile is formed in a multi buffered solution that contains a mixture of buffers having a plurality of protonation states with various charges, for example two or three. For brevity, $A_i^{-2}$ and $AH_i^-$ denotes two-state buffers for negatively charged species, $B_j^+$ and $BH_j^{+2}$ denotes two-state buffers for positively charges species, $Ka_i$ and $Kb_j$ denotes respective equilibrium constants, where i and j denotes buffer indices, $A_{D,k}^{-3}$, $A_DH_k^{-2}$ and $A_DH_{2,k}^-$ denotes three-state buffers with equilibrium constants $Ka_{D,k}^1$, $Ka_{D,k}^2$, and $B_{D,l}^+$, $B_DH_l^{+2}$ and $B_DH_{2,l}^{+3}$ denotes three-state buffers with equilibrium constants $Kb_{D,k}^1$ and $Kb_{D,k}^2$ where k and l denotes buffer indices. It should be noted that each one of the buffer species is either positively or negatively charged, as further described below. The protonation reaction of these buffers may be defined as follows:

$$H^+ + OH^- \Leftrightarrow H_2O,$$

$$A_i^{-2} + H^+ \Leftrightarrow AH_i^-,$$

$$B_j^+ + H^+ \Leftrightarrow BH_j^{+2},$$

$$A_{D,k}{}^{-3} + H^+ \Leftrightarrow A_DH_k{}^{-2},$$

$$A_DH_k{}^{-2} + H^+ \Leftrightarrow A_DH_{2,k}{}^-,$$

$$B_{D,l}{}^+ + H^+ \Leftrightarrow B_DH_l{}^{+2},$$

$$B_DH_l{}^{+2} + H^+ \Leftrightarrow B_DH_{2,l}{}^{+3}. \quad \text{Equation 15:}$$

The equation system is composed of the following mass balances:

$$j^I_{OH} - j^I_{H_2O} = j^{III}_{H_2O} + j^{III}_{OH}, \quad \text{Equation 16}$$

$$-2\sum_k J^I_{A_DH_{2,k}} + 2\sum_l J^I_{B_DH_{2,l}} - \sum_k J^I_{A_DH_k} +$$

$$\sum_l J^I_{B_DH_l} - \sum_i J^I_{AH_i} + \sum_j J^I_{BH_j} + J^I_H + J^I_{H_2O}, =$$

$$J_H + J^{III}_H - J^{III}_{H_2O} - \sum_i J^{III}_{AH_i} + \sum_j J^{III}_{BH_j} - \sum_k J^{III}_{A_DH_k} +$$

$$\sum_l J^{III}_{B_DH_l} - 2\sum_k J^{III}_{A_DH_{2,k}} + 2\sum_l J^{III}_{B_DH_{2,l}},$$

$$J^I_{A_i} + J^I_{AH_i} = J^{III}_{A_i} + J^{III}_{AH_i},$$

$$J^I_{B_j} + J^I_{BH_j} = J^{III}_{B_j} + J^{III}_{BH_j},$$

$$J^I_{A_{D,k}} + J^I_{A_DH_k} + J^I_{A_DH_{2,k}} = J^{III}_{A_{D,k}} + J^{III}_{A_DH_k} + J^{III}_{A_DH_{2,k}},$$

$$J^I_{B_{D,l}} + J^I_{B_DH_l} + J^I_{B_DH_{2,l}} = J^{III}_{B_{D,l}} + J^{III}_{B_DH_l} + J^{III}_{B_DH_{2,l}},$$

and low of mass actions:

$$K_W = [H^+]^{I,III} \cdot [OH^-]^{I,III}$$

$$Ka_i = [A_i^{-2}]^{I,III} \cdot [H^+]^{I,III}/[AH_i^-]^{I,III},$$

$$Kb_j = [B_j^+]^{I,III} \cdot [H^+]^{I,III}/[BH_j^{+2}]^{I,III},$$

$$Ka_{D,k}^1 = [A_{D,k}^{-3}]^{I,III} \cdot [H^+]^{I,III}/[A_DH_k^{-2}]^{I,III},$$

$$Ka_{D,k}^2 = [A_DH_k^{-2}]^{I,III} \cdot [H^+]^{I,III}/[A_DH_{2,k}^-]^{I,III},$$

$$Kb_{D,l}^1 = [B_{D,l}^+]^{I,III} \cdot [H^+]^{I,III}/[B_DH_l^{+2}]^{I,III},$$

$$Kb_{D,l}^2 = [B_DH_l^{+2}]^{I,III} \cdot [H^+]^{I,III}/[B_DH_{2,l}^{+3}]^{I,III}, \quad \text{Equation 17:}$$

with:

$$J_{A_i}^{I,III} = v_{A_i} \cdot [A_i^{-2}]^{I,III}, J_{AH_i}^{I,III} = v_{AH_i} \cdot [AH_i^-]^{I,III}, J_{B_j}^{I,III} = v_{B_j} \cdot [B_j^+]^{I,III}, J_{BH_j}^{I,III} = v_{BH_j} \cdot [BH_j^{+2}]^{I,III},$$

$$J_{A_{D,k}}^{I,III} = v_{A_{D,k}} \cdot [A_{D,k}^{-3}]^{I,III}, J_{A_DH_k}^{I,III} = v_{A_DH_k} \cdot [A_DH_k^{-2}]^{I,III}, J_{A_DH_{2,k}}^{I,III} = v_{A_DH_{2,k}} \cdot [A_DH_{2,k}^-]^{I,III},$$

$$J_{B_{D,l}}^{I,III} = v_{B_{D,l}} \cdot [B_{D,l}^+]^{I,III}, J_{B_DH_l}^{I,III} = v_{B_DH_l} \cdot [B_DH_l^{+2}]^{I,III}, J_{B_DH_{2,l}}^{I,III} = v_{B_DH_{2,l}} \cdot [B_DH_{2,l}^{+3}]^{I,III} \quad \text{Equation 18:}$$

Solving these equations using numerical methods gives, similarly to the described above, necessary parameters as maximum injection current, maximum focusing pH ramp etc. It should be noted that the solution of these algebraic equations (Equations 16-18) allows calculating one or more pH ramps, as described above. In such a manner, a calculation of partial differential equations, such as equation 1 and 2, may be avoided and the therefore the computational complexity of the calculation process is reduced.

Figure 13:
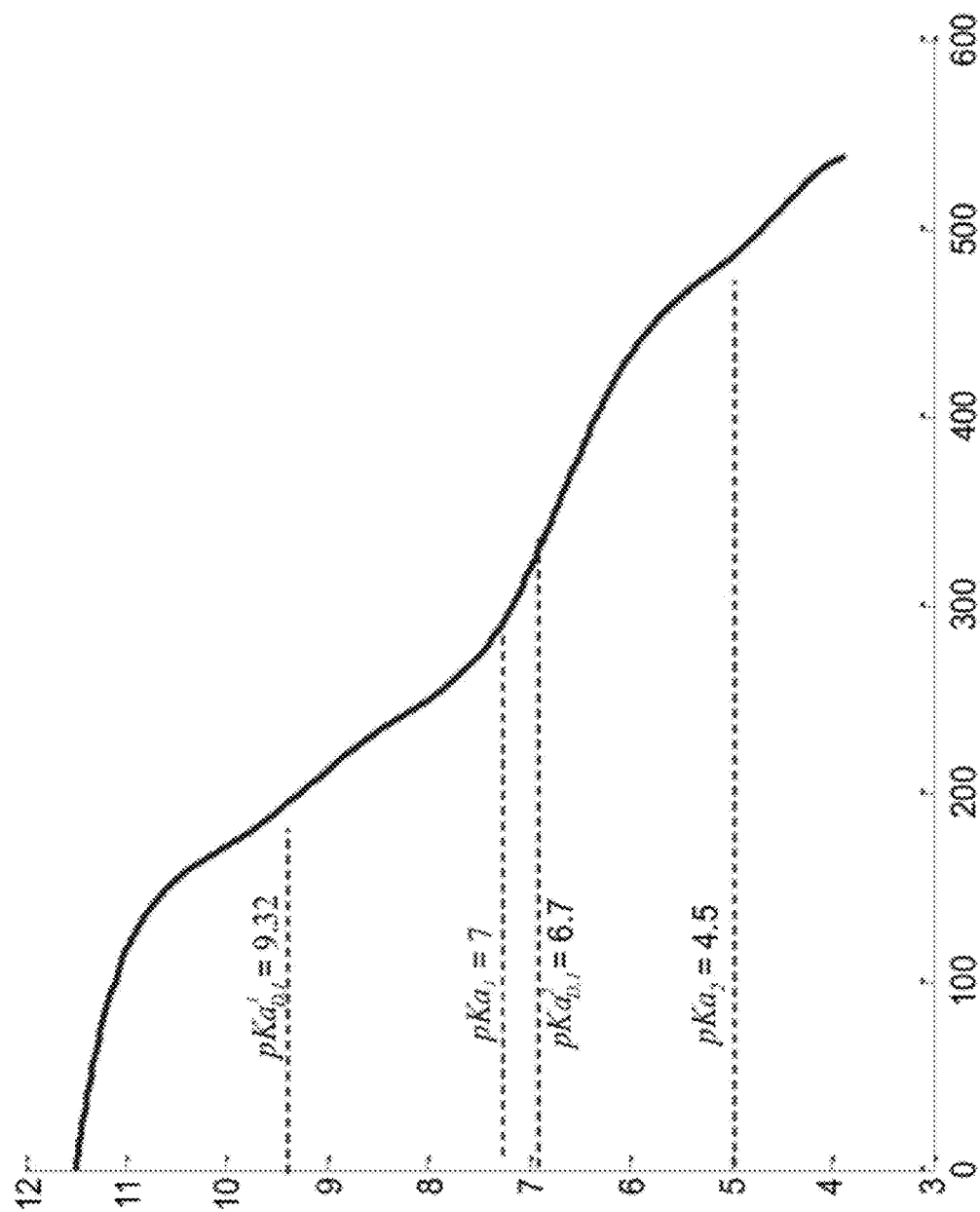
FIG. 13 is a graph depicting the correlation between change in the electric current and the pH in a solution having three buffers, two of them having two protonation states, and one having three protonation states, according to some embodiments of the present invention.

FIG. 13 depicts a simulation of three buffers, two of them having two protonation states, and one having three protonation states. The various equilibrium constants are indicated. Since three buffers are involved, the pH profile resides on a broad range that facilitates the production of various focusing pH ramps at various points. With these kinds of mixtures, various dynamic pH profiles may be efficiently established.

Reference is now made to a process of selecting an electrolyte solution for a separation volume, according to some embodiments of the present invention. Electrolytes may be divided into two main groups: buffer molecules, which undergo reaction in the separation volume, for example in the container 102, and supporting ions, acting as a background medium.

In order to facilitate molecular analyte migration the protonation states of the buffered solution should be charged in the pH range defined by all the zones of the dynamic pH profile. In such a manner, a steady state in a pH ramp may be reached and ion fluxes in the container 102 are maintained by the applied electric field. When the buffered solution is charged, species move along the pH profile with no accumulation over time. Neutral molecules, in contrast, are not influenced by the field and diffuse slowly to both directions, increasing considerably the time to reach a steady state.

In order to facilitate volume separation, the buffer in the container 102 is selected as to cover the entire pH range of the estimated pH profile. Furthermore, it was previously shown in FIGS. 12 and 13 that the device's resistance to current, varies over the pH range. That is, the resulting ΔpH for a given increase in injection current density is pH dependent.

Figure 14:
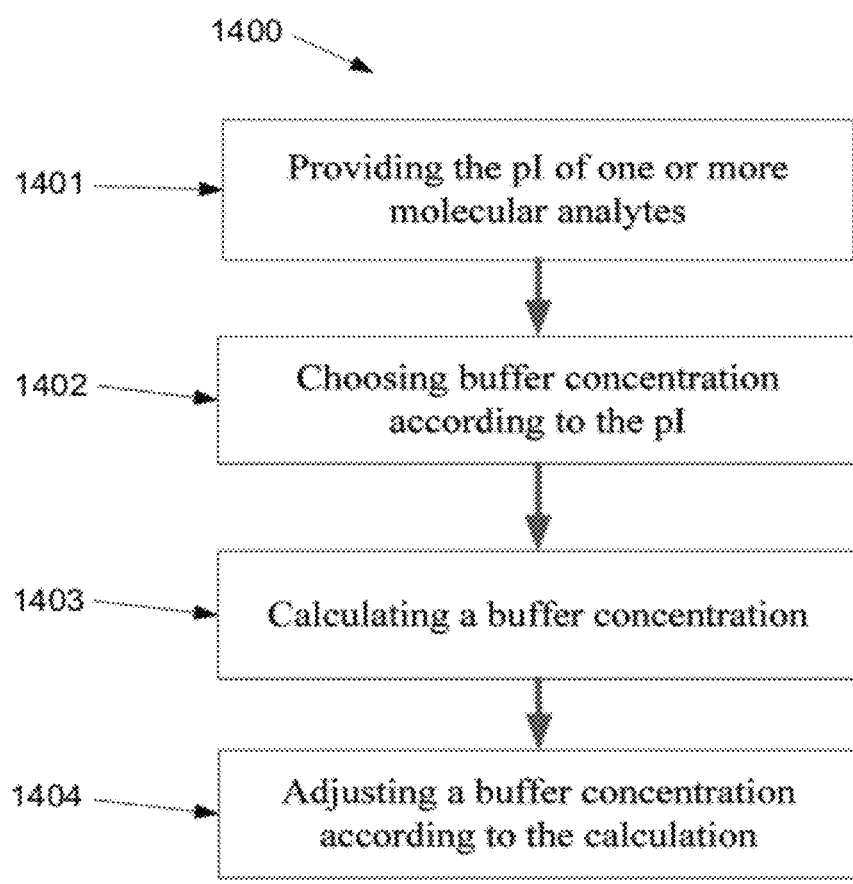
FIG. 14 is a flowchart 1400 of a method of setting a buffered solution for one or more molecular analytes, according to some embodiments of the present invention.

Reference is now made to FIG. 14, which is a flowchart 1400 of a method of setting a buffered solution for one or more molecular analytes, for example for a certain mixture of molecular analytes, according to some embodiments of the present invention. The buffer elements may be pyrophosphate, phosphate, histidine, citrate, carbonate, BIS-TRIS propane, and/or the like.

First, as shown at 1401, the pI of one or more molecular analytes in a probed mixture is provided. Than, as shown at 1402, a buffer is selected according to the received pI(s). Now, as shown at 1403, buffer concentration and type is chosen, for example computed or selected according to the received pI(s). The buffer concentration is calculated while taking into account that a high buffer concentration requires ion sources with a high current and a low buffer concentration may form an unstable pH ramp that is not stable to current fluctuations.

For example, if a mixture contains protein with pI's between 5 and 7, the appropriate electrolyte should contain at least one buffer with pKa in a respective range, or close enough to it. In addition, the total concentration of this buffer should be high enough so that the inevitable fluctuations in ion injections would not have a strong effect on the stability of the pH ramp. To keep the model described above accurate, electrical properties along the container 102, for example conductivity, are maintained constant. In such a manner, electrical properties of the solution in the container 102 remain suitable for generating a dynamic pH profile that stably and/or predictably induces molecular analytes migration, for example as described above. In the absence of such supporting ions, a difference in conductivity between the two sides of a pH ramp zone is expected due to different ion profiles. Adding supporting ions, referred to herein as supporting electrolyte, in a certain concentration reduces conductivity difference in the separation solution, hence making the model predictions more accurate. However, when the concentration is increased above a certain threshold, undesirable heating of the container 102 may be induced. When choosing the appropriate supporting electrolyte, the total ion strength of the container 102, the magnitude of the applied electric field, and the dimensions of the container 102 should be taken into account. For example a possible recipe for an electrolyte, suitable for implementation in the pH range of 11.5-4 is:

| Buffer | Concentration (M) |
|---|---|
| phosphate | 0.004 |
| Citrate | 0.004 |
| Pyrophsphate | 0.007 |
| Sodium sulfate | 0.013 |
| NaOH, Na2SO4 | Adjustment to desired pH |

Now, as shown at 1404, a buffered solution with a buffer concentration which is set for the process of separating two or more molecular analytes is set according to 1402. The setting of the buffer concentration is made so as to make the solution more pH resistant and thus more stable to fluctuations which are induced by the aforementioned ion injection.

It is expected that during the life of a patent maturing from this application many relevant methods and systems will be developed and the scope of the term a controller, a sensor and a computing unit is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or ramps, but only if the additional ingredients and/or ramps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of separating a mixture of a plurality of tool molecular analytes having different isoelectric points (pIs), comprising:
    placing a solution containing a mixture of a plurality of molecular analytes in separation volume;
    trapping said plurality of molecular analytes in between at least two pH step zones in a separation volume containing said solution, each said pH step zone having a different substantially uniform pH; and
    a plurality of ion sources distributed along a longitudinal axis of said separation volume configured to inject ions in a controlled manner across said longitudinal axis of said separation volume to gradually change a pH in at least one of said two pH step zones and to induce a sequential migration of said plurality of molecular analytes along said longitudinal axis toward a common point in a plurality of separate drifting bands each having a different pIs; and
    separately performing at least one of harvesting and diagnosing each one of said plurality of drifting bands from said common point.

2. The method of claim 1, wherein said injection comprises generating a pH profile having a plurality of pH zones including said at least two pH step zones in said separation volume, and changing the pH in one of said at least two pH step zones.

3. The method of claim 1, wherein said injecting changes gradually as a function of time.

4. The method of claim 2, wherein said pH profile is defined by at least one ramp, said plurality of molecular analytes accumulating in said at least one ramp.

5. The method of claim 2, wherein said generating comprises applying an electric field on said solution along said longitudinal axis, and injecting a plurality of ion flows in a plurality of points along said longitudinal axis to establish said pH profile.

6. The method of claim 2, further comprising adding at least one buffer element to said solution so as to stabilize said pH profile.

7. The method of claim 1, wherein said harvesting further comprises collecting molecular analytes of a first of said plurality of separate drifting bands while said molecular analytes of a second of said plurality of separate drifting bands remain in said separation volume.

8. The method of claim 1, wherein said sequential migration comprises inducing a migration of first and second separate drifting bands of molecular analytes from said plurality of separate drifting bands in opposite directions along said longitudinal axis.

9. The method of claim 2, wherein said injecting comprises adjusting said pH profile to change a direction of said migration along said longitudinal axis so that said plurality of separate drifting bands of molecular analytes sequentially drift in two opposing directions.

10. The method of claim 2, wherein during said trapping said plurality of pH zones having two step zones having a substantially uniform first pH separated by a middle step zone having a substantially uniform second pH, said mixture being trapped in between one of said two step zones and said middle step zone, said injecting comprising changing the pH in said middle step zones.

11. The method of claim 2, wherein said plurality of pH zones comprises at least three different pH zones, said injecting being performed to induce a migration of a first of said plurality of separate drifting bands to a first ramp zone between a first pair of said plurality of pH zones and a second of said plurality of separate drifting bands to a second ramp zone between a second pair of said plurality of pH zones.

12. The method of claim 1, wherein said solution is buffered.

13. The method of claim 12, further comprising:
providing an isoelectric point of one or more molecular analytes in said mixture and setting said solution according to said isoelectric point;
determining a buffer concentration of said solution according to said isoelectric point; and
setting said solution according to said determining.

14. The method of claim 1, wherein said injecting comprise focusing first and second of said plurality of separate drifting bands apart from one another along said longitudinal axis.

15. The method of claim 14, further comprising separately collecting said first and second separate drifting bands from different locations along said longitudinal axis.

16. The method of claim 2, wherein said injecting comprises calculating at least one adjustment for said pH profile according to a set of algebraic equations and performing said adjusting according to said at least one adjustment.

17. The method of claim 1, wherein said trapping comprises applying an electric field on said solution and injecting a plurality of ion flows in at least one point along to establish said two pH step zones.

18. A method of separating molecular analytes based on their isoelectric point, comprising:
generating a pH profile having a plurality of pH zones along a longitudinal axis of a separation volume that includes a solution having a plurality of molecular analytes;
providing a plurality of ion sources distributed along said longitudinal axis configured to gradually change the profile of said pH profile over a period by inducing a migration of said plurality of molecular analytes along said longitudinal axis toward a common point in a plurality of separate drifting bands each having a different pI; and
separately performing at least one of harvesting and diagnosing each one of said plurality of drifting bands from said common point.

19. A device for separating a mixture of a plurality of molecular analytes having different isoelectric points (pIs), comprising:
a container sized and shaped configured to contain a solution having a plurality of molecular analytes along a longitudinal axis;
an electric source configured to apply an electric field along said longitudinal axis of said container in said solution;
a plurality of ion sources distributed along said longitudinal axis configured to establish a pH profile along said longitudinal axis in said solution by injecting in a controlled manner a plurality of ion flows to at least one of protonating and deprotonating a plurality of zones of said solution;
a controller configured to operate said plurality of ion sources to adjust said pH profile to trap said plurality of molecular analytes in between at least two pH step zones in said container, each said pH step zone having a different substantially uniform pH, said controller configured to operate said plurality of ion sources to gradually adjust said pH profile so as to induce a migration of said plurality of molecular analytes in a plurality of separate drifting bands along said longitudinal axis toward a common point, each one of said plurality of separate drifting bands has a different pIs; and
a unit configured to separately performs at least one of harvesting and diagnosing of each one of said plurality of drifting bands from said common point.

20. The device of claim 19, further comprising an interface configured to receive a plurality of instructions from at least one of a computing unit and a user, said controller configured to operate said plurality of ion sources according to said plurality of instructions.

21. The device of claim 19, wherein said container having at least one dimension of less than one millimeter.

22. The device of claim 19, wherein said solution is a non gel solution.

* * * * *